(12) United States Patent
Carpino et al.

(10) Patent No.: US 9,975,870 B2
(45) Date of Patent: May 22, 2018

(54) 5,6-DIMETHOXY-1,1-DIOXOBENZO[B] THIOPHENE-2-METHYLOXYCARBONYL (DM-BSMOC) AND RELATED AMINO-PROTECTING GROUPS

(71) Applicant: MASSACHUSETTS, UNIVERSITY OF, Boston, MA (US)

(72) Inventors: Louis A. Carpino, Amherst, MA (US); Adel A. Abdel-Maksoud, Amherst, MA (US); Hesham A. Ahmed, Amherst, MA (US); Calin Dan Sferdean, Ann Arbor, MI (US)

(73) Assignee: MASSACHUSETTS, UNIVERSITY OF, Boston, MA (US)

( * ) Notice: Subject to any disclaimer, the term of this patent is extended or adjusted under 35 U.S.C. 154(b) by 0 days. days.

(21) Appl. No.: 14/905,261

(22) PCT Filed: Jul. 16, 2014

(86) PCT No.: PCT/US2014/046867
§ 371 (c)(1),
(2) Date: Jan. 14, 2016

(87) PCT Pub. No.: WO2015/009837
PCT Pub. Date: Jan. 22, 2015

(65) Prior Publication Data
US 2016/0152591 A1 Jun. 2, 2016

Related U.S. Application Data

(60) Provisional application No. 61/847,022, filed on Jul. 16, 2013.

(51) Int. Cl.
*C07D 333/52* (2006.01)
*C07D 333/64* (2006.01)
*C07D 409/12* (2006.01)
*C07D 333/56* (2006.01)
*C07D 413/12* (2006.01)

(52) U.S. Cl.
CPC ......... *C07D 333/64* (2013.01); *C07D 333/56* (2013.01); *C07D 409/12* (2013.01); *C07D 413/12* (2013.01); *Y02P 20/55* (2015.11)

(58) Field of Classification Search
CPC .. C07D 333/64; C07D 333/56; C07D 409/12; C07D 413/12; Y02P 20/55
USPC .......................................................... 549/51
See application file for complete search history.

(56) References Cited

PUBLICATIONS

Small, P. W. et al., "Design and Application of a New Rigid Support for High Efficiency Continuous-flow Peptide Synthesis", Journal of the Chemical Society Chemical Communications, Jan. 1989, vol. 21, p. 1589-1591, ISSN 0929-8665.

Gundala, C. et al., "Synethsis of 1,1-Dioxobenzo[b] thiophene-2-ylmethyloxy carbonyl (Bsmoc) Protected N-Methyl Amino Acids by Reduction of Bsmoc-5-Oxazolidinones and Their Use in Peptide Synthesis", Protein & Peptide Letters, 2009, vol. 16, p. 105-111, ISSN 0022-4936.

*Primary Examiner* — Taylor V Oh
(74) *Attorney, Agent, or Firm* — Lando & Anastasi, LLP

(57) ABSTRACT

Amino acid protecting groups are provided for use in peptide synthesis. Particular compounds disclosed include 5,6-dimethoxy-1,1-dioxobenzo[b]thiophi methyloxycarbonyl (DM-Bsmoc) and related amino-protecting groups.

4 Claims, 5 Drawing Sheets

5,6-DIMETHOXY-1,1-DIOXOBENZO[B]THIOPHENE-2-METHYLOXYCARBONYL (DM-BSMOC) AND RELATED AMINO-PROTECTING GROUPS

CROSS-REFERENCE TO RELATED APPLICATIONS

This application is a U.S. national phase application and claims the benefit of priority under 35 U.S.C. § 371 of International (PCT) Patent Application Serial No. PCT/US2014/046867 filed on Jul. 16, 2014 which, in turn, claims priority under 35 U.S.C. § 119(e) to U.S. Provisional Patent Application Serial No. 61/847,022 filed on Jul. 16, 2013.

FIELD OF THE DISCLOSURE

The present disclosure relates to amino protecting groups for the synthesis of peptides.

SUMMARY

Certain embodiments of the disclosure provide for an amino acid protecting group capable of being coupled to a primary or secondary amine. The protecting group comprises 5,6-dimethoxy-1,1-dioxobenzo[b]thiophene-2-methyloxycarbonyl (DM-Bsmoc). The DM-Bsmoc group may be introduced via a chloroformate or an N-succimidyl ester (OSu).

Certain embodiments of the disclosure provide for an amino acid protecting group capable of being coupled to an amino acid, the amino acid protecting group having a chemical formula of:

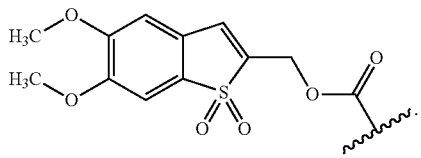 [SMILES: *C(=O)OCC1=Cc2cc(OC)c(OC)cc2S1(=O)=O]

Certain embodiments of the disclosure provide for an α-protected amino acid compound having a chemical formula:

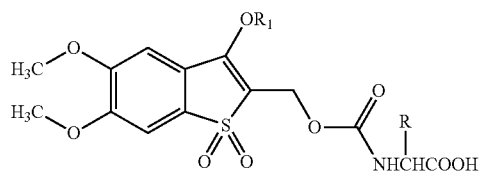

wherein R is a functional group of an amino acid and $R_1$ is selected from the group consisting of Me-, MeOCH$_2$CH$_2$—, and MeO(CH$_2$CH$_2$O)nCH$_2$CH$_2$—.

In yet other embodiments, an amino protecting group is provided having a chemical formula of

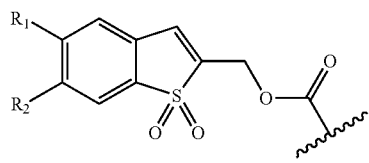

wherein $R_1$ and $R_2$ are one of the following:
$R_1$=MeO, $R_2$=OCH$_2$CH$_2$OMe
$R_1$=OCH$_2$CH$_2$OMe, $R_2$=MeO
$R_1$=MeO, $R_2$=OCH$_2$SO$_3$K
$R_1$=OCH$_2$SO$_3$K, $R_2$=MeO
$R_1$=MeO, $R_2$=MeO
$R_1$=lower alkyl-O, $R_2$=lower alkyl-O
$R_1$=MeSO$_2$, $R_2$=H
$R_1$=H, $R_2$=MeSO$_2$
$R_1$=$R_2$=MeSO$_2$
$R_1$=MeO, $R_2$=MeO(CH$_2$CH$_2$O)n
$R_1$=MeO(CH$_2$CH$_2$O)n, $R_2$=MeO
$R_1$=Me$_3$N$^+$, $R_2$=H
$R_1$=H, $R_2$=Me$_3$N$^+$
$R_1$=MeO, $R_2$=MeSO$_2$
$R_1$=MeSO$_2$, $R_2$=MeO
$R_1$=Cl, $R_2$=H
$R_1$=H, $R_2$=Cl
$R_1$=Cl, $R_2$=Cl.

In yet other embodiments of the disclosure, an α-protected amino acid compound is provided having a chemical formula of:

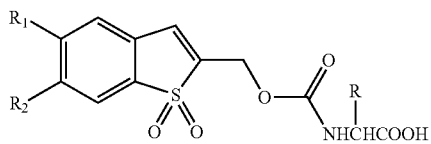

wherein $R_1$ and $R_2$ are one of the following:
$R_1$=MeO, $R_2$=OCH$_2$CH$_2$OMe
$R_1$=OCH$_2$CH$_2$OMe, $R_2$=MeO
$R_1$=MeO, $R_2$=OCH$_2$SO$_3$K
$R_1$=OCH$_2$SO$_3$K, $R_2$=MeO
$R_1$=MeO, $R_2$=MeO
$R_1$=lower alkyl-O, $R_2$=lower alkyl-O
$R_1$=MeSO$_2$, $R_2$=H
$R_1$=H, $R_2$=MeSO$_2$
$R_1$=$R_2$=MeSO$_2$
$R_1$=MeO, $R_2$=MeO(CH$_2$CH$_2$O)n
$R_1$=MeO(CH$_2$CH$_2$O)n, $R_2$=MeO
$R_1$=Me$_3$N$^+$, $R_2$=H
$R_1$=H, $R_2$=Me$_3$N$^+$
$R_1$=MeO, $R_2$=MeSO$_2$
$R_1$=MeSO$_2$, $R_2$=MeO
$R_1$=Cl, $R_2$=H
$R_1$=H, $R_2$=Cl
$R_1$=Cl, $R_2$=Cl.
and wherein R is a functional group of an amino acid.

The α-protected amino acids of the embodiments described may comprise amino acids selected from the group consisting of arginine (Arg), histidine (His), lysine (Lys), aspartic acid (Asp), glutamic acid (Glu), serine (Ser), threonine (Thr), asparagine (Asn), glutamine (Gln), cysteine (Cys), glycine (Gly), proline (Pro), alanine (Ala), isoleucine (Be), leucine (Leu), methionine (Met), phenylalanine (Phe), tryptophan (Trp), tyrosine (Tyr), valine (Val), and modifications thereof. The α-protected amino acids of the embodiments described may also comprise amino acids such as pyrrolysine (Pyl) and hydroxyproline.

Methods may also be provided in certain embodiments. A method of preparing an amino acid protecting group comprising 5,6-dimethoxy-1,1-dioxobenzo[b]thiophene-2- methyloxycarbonyl is provided comprising preparing the amino acid protecting group from an intermediate compound comprising A method of preparing an α-protected amino acid is provided comprising bonding an amino acid to a chemical compound of the formula:

A method of preparing an α-protected amino acid is also provided comprising bonding an amino acid to a chemical compound of the formula:

DM-BsmocOSu

In certain embodiments, a composition is provided comprising a depsidipeptide from DM-Bsmoc-Ala-OH and Boc-Thr-OH, having a chemical compound of the formula:

DM-Bsmoc-Ala⌐
Boc-Thr-OH

In certain embodiments, a composition is provided comprising a pseudo-proline dipeptide from DM-Bsmoc-Ala-OH and a threonine-based pseudo-proline, having a chemical compound of the formula:

In certain embodiments, a method of assembling peptides on a solid phase support according to the Merrifield technique is provided using DM-Bsmoc amino acids.

In certain embodiments, a method of preparing a peptide is provided. The method comprises providing a solid support capable of attaching an amino acid. The method also comprises coupling an α-protected amino acid compound having an α-protecting group bonded to an amino acid, the α-protected amino acid compound having a chemical formula of:

wherein $R_1$ and $R_2$ are one of the following:
$R_1$=MeO, $R_2$=OCH$_2$CH$_2$OMe
$R_1$=OCH$_2$CH$_2$OMe, $R_2$=MeO
$R_1$=MeO, $R_2$=OCH$_2$SO$_3$K
$R_1$=OCH$_2$SO$_3$K, $R_2$=MeO
$R_1$=MeO, $R_2$=MeO
$R_1$=lower alkyl-O, $R_2$=lower alkyl-O
$R_1$=MeSO$_2$, $R_2$=H
$R_1$=H, $R_2$=MeSO$_2$
$R_1$=$R_2$=MeSO$_2$
$R_1$=MeO, $R_2$=MeO(CH$_2$CH$_2$O)n
$R_1$=MeO(CH$_2$CH$_2$O)n, $R_2$=MeO
$R_1$=Me$_3$N$^+$, $R_2$=H
$R_1$=H, $R_2$=Me$_3$N$^+$
$R_1$=MeO, $R_2$=MeSO$_2$
$R_1$=MeSO$_2$, $R_2$=MeO
$R_1$=Cl, $R_2$=H;
$R_1$=H, $R_2$=Cl; and
$R_1$=Cl, $R_2$=Cl.
and wherein R is functional group of an amino acid, to the solid support. The method also comprises deprotecting the α-amino acid protecting group from the amino acid.

In certain embodiments, a composition comprising leucine enkephalin, prepared by solid phase synthesis using 5,6-dimethoxy-1,1-dioxobenzo[b]thiophene-2-methyloxycarbonyl (DM-Bsmoc) is provided.

In certain other embodiments, a composition comprising ACP$^{65-74}$ (Acyl Carrier Protein (H-VAL-GLN-ALA-ALA-ILE-ASP-TYR-ILE-ASN-GLY-OH)), prepared by solid phase synthesis using 5,6-dimethoxy-1,1-dioxobenzo[b]thiophene-2-methyloxycarbonyl (DM-Bsmoc) is provided.

BRIEF DESCRIPTION OF THE DRAWINGS

The features, aspects and advantages of the present invention will become better understood upon consideration of the following drawings in which.

Figure 1:
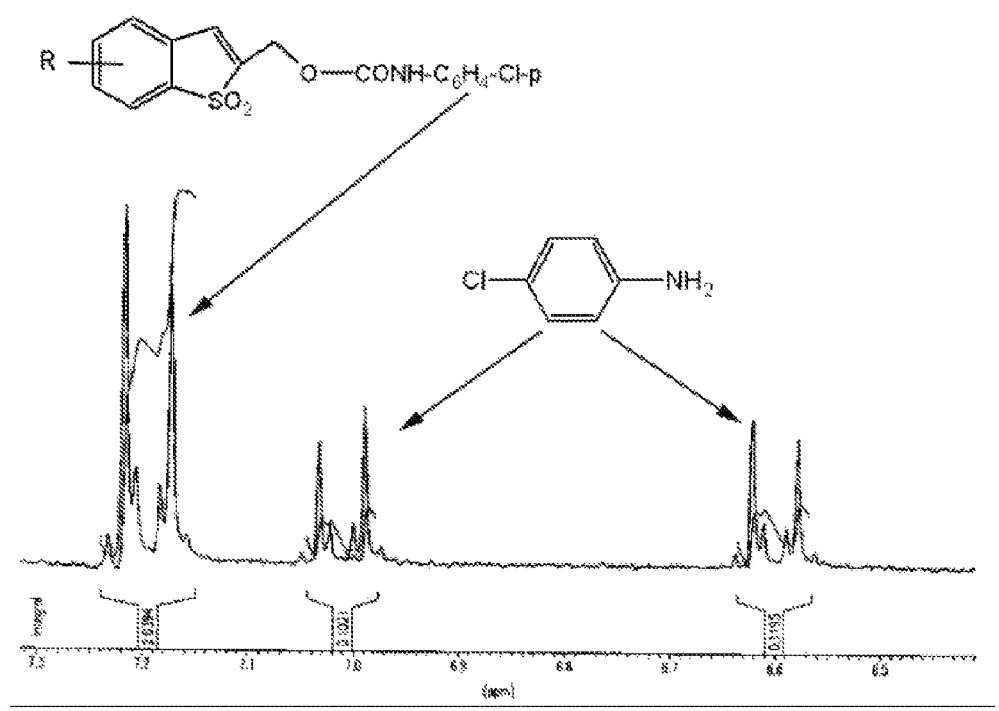
FIG. 1 depicts a snapshot for the progress of the deblocking process for a mixture of R-Bsmoc-PCA and piperidine according to $^1$H-NMR Analysis.

It should be understood that these drawings are not necessarily to scale and that details which may not be necessary or which render other details difficult to perceive may have been omitted. It should also be understood that the invention is not limited to the particular embodiments illustrated herein.

DETAILED DESCRIPTION

Among the many α-amino protecting groups which have been devised for the synthesis of peptides, three stand out as being of special utility, the benzyloxycarbonyl, t-butyloxycarbonyl and 9-fluorenylmethyloxycarbonyl groups (Z, Boc and Fmoc). The α-amino protecting group may also be referred to as an α-(protected amino) acid group or an α-amino protected amino acid, or a protected α-amino acid. For peptide assembly a simple amino acid α-protected by one of these groups is coupled to a free amino acid ester, the α-amino acid protectant is then removed by a deblocking process and a $2^{nd}$ similarly-protected amino acid is then coupled to the free amino function and the process is continued until the desired peptide sequence is complete. Finally the C-terminal ester function and any side-chain protecting groups are removed to give the desired free unprotected peptide. In this way a desired sequence can be built by either a solution or solid phase (Merrifield) technique. Of the three groups cited, the Fmoc group has become the overwhelming choice of the majority of peptide practitioners due to the ease of its deblocking by treatment with the mild secondary amine piperidine. In contrast, less convenient deblocking techniques are required for the Z (catalytic hydrogenolysis or strong acid) or Boc (trifluoroacetic acid) functions. Especially in the case of the solid phase technique carried out on an automated peptide synthesizer has the Fmoc group been chosen for nearly all such syntheses.

Urethane protecting groups such as Cbz, Fmoc, and Bsmoc have been extensively used for the protection of primary and secondary amines in chemical synthesis. In particular the urethane protecting group, Fmoc has been extensively applied as a chemical protecting group for primary and secondary amines in a wide array of chemical structures. This includes protection of primary and secondary amino acids used for peptide synthesis as well as protection of many primary and secondary amines used in peptidomimetic synthesis such as azapeptides, beta-peptides, peptoids and peptide nucleic acids (PNA) among others. In recent years the use of non-standard amino acids has attracted great interest due to their potential increased stability in-vivo as well as their ability to uniquely affect the properties of a synthesized molecule. There are now many commercially available primary and secondary amines protected with urethane protecting groups. Therefore, it has been demonstrated that urethane protecting groups can potentially be used to protect almost any primary or secondary amine.

An analog of the Fmoc group which is deblocked under even milder conditions by the same reagent piperidine, the 1,1-dioxobenzo[b]thiophene-2-methyloxycarbonyl (Bsmoc) group, was reported in 1997 but has never been commercialized in spite of its many advantages. Among the advantages of Bsmoc chemistry over Fmoc chemistry in addition to the greater ease of deblocking via Michael addition (Bsmoc) rather than β-elimination (Fmoc) which results in the formation of fewer base-catalyzed side reactions are the following:

1—It has been found through development of the present disclosure that the Bsmoc residue which bears a more hydrophilic sulfone residue as opposed to the very hydrophobic Fmoc residue enhances water solubility and is less subject to aggregation effects which interfere with the assembly of a desired peptide chain especially during application of the solid phase methodology.

2—It has been found through development of the present disclosure that the reactivity during the coupling step of Bsmoc amino acids is enhanced relative to that of the Fmoc analogs possibly due to a combination of steric and inductive effects.

3—It has been found through development of the present disclosure that by virtue of its being a Michael addition process the deblocking step involving the Bsmoc residue can be carried out via a non-basic but highly effective nucleophile and thus avoid side reactions induced by the presence of a basic reagent.

However in spite of these advantages Bsmoc chemistry has not only not displaced the less effective Fmoc system but has indeed never even competed with it primarily because only about half of the proteinogenic Bsmoc-protected amino acids can be isolated in the form of stable easily crystallized compounds, the others being oily substances or amorphous materials which are only inconveniently handled and therefore not commercially viable. Those amino acids that are found to form stable easily crystallized compounds include Gly, Ala, Val, Phe, Thr(tBu), Tyr(t-Bu), Asn(Trt), Gln(Trt), Arg(Pbf), His(Trt), and Trp. The oily substances or amorphous materials may include amino acids such as Asp(O-t-Bu), Pro, Be, Leu, Met, Lys(Boc), Ser(t-Bu), Cys(Trt), and Glu(O-t-Bu).

In the present disclosure we describe a substituted Bsmoc residue, the 5,6-dimethoxy-Bsmoc group for which all such protected amino acids, previously obtainable in Bsmoc form only as oils or amorphous materials, can now be obtained in the form of stable solids. Without wishing to be bound by theory, this effect may be due to the symmetrical structure of the 5,6-dimethoxy substituted benzo[b]thiophene ring system. Thus, in some embodiments, peptide syntheses may be achieved easily using Bsmoc chemistry via a mixture of ordinary Bsmoc amino acids and the DM-Bsmoc amino acids. In certain embodiments, peptide syntheses can be carried out completely using only DM-Bsmoc amino acids. Having such a protocol available is especially important in the case of syntheses of peptides on an industrial scale as in the synthesis and development of new peptide-based drugs for medicinal use. In addition, because of the presence of the two methoxy substituents the new DM-Bsmoc amino acids can be more water soluble than the original Bsmoc amino acids and thus can be more suitable for new environmentally-friendly procedures whereby the work-up can be switched from an organic to an aqueous-based system. Thus, with Fmoc chemistry the coupling and deblocking steps are carried out in a solvent such as dimethylformamide (DMF) or N-methylpyrrolidone (NMP) and then the same solvents mixed with other organic solvents are used to wash the resins (e.g., a solid support) to remove excess starting materials or by-products. Such a process generates large volumes of organic solvents which must be disposed of or recovered. It has already been shown that the parent Bsmoc residue can be used in such a modified process involving the use of DMF or NMP only for the actual coupling or deblocking steps whereas in the washing steps the DMF or NMP can be replaced by aqueous alcohol mixtures thus greatly reducing the organic solvent footprint. In the case of the DM-Bsmoc system this situation is further improved due to the enhanced water solubility of these systems.

Fortunately, for a set of amino acid derivatives destined to become available commercially on a large scale the synthesis of the DM-Bsmoc amino acids can begin with a very inexpensive starting material, namely veratraldehyde 1 which is brominated in high yield to give 2 which upon treatment with ethyl mercaptoacetate in the presence of potassium carbonate gives ester 3. Other facile and inexpensive methods of forming the benzo[b]thiophene ring system are also available such as the reaction of the cinnamic acid with thionyl chloride. Upon Vitride reduction 3 is converted to the sulfide alcohol 4 which upon oxidation via treatment with monoperoxyphthalic acid magnesium salt hexahydrate (MMPP) gives the sulfone alcohol 5 which represents the key intermediate in the synthesis of the DM-Bsmoc amino acids. Treatment of 5 with triphosgene gives the chloroformate 6 which can then be used to introduce the DM-Bsmoc residue onto the proteinogenic amino acids by the Bolin technique (Bolin D R, Sytwu I I, Humiec F, Meienhofer J. Int J Pept Protein Res. 1989; 33:353) or be converted to the corresponding OSu ester (DM-Bsmoc-OSu) which then can be used to acylate the amino acid. Any amino acid or other related compound may be coupled to, bonded to, or reacted with the chloroformate or the OSu ester (DM-Bsmoc-OSu), or other modified DM-Bsmoc proctecting group as described in this disclosure, to provide an α-protected amino acid that may be used for peptide synthesis or other process. Bonding may occur by way of covalent or ionic bonds, or by way of a coupling reaction. Other reagents for the introduction of the DM-Bsmoc group onto an amino acid or other molecule may include

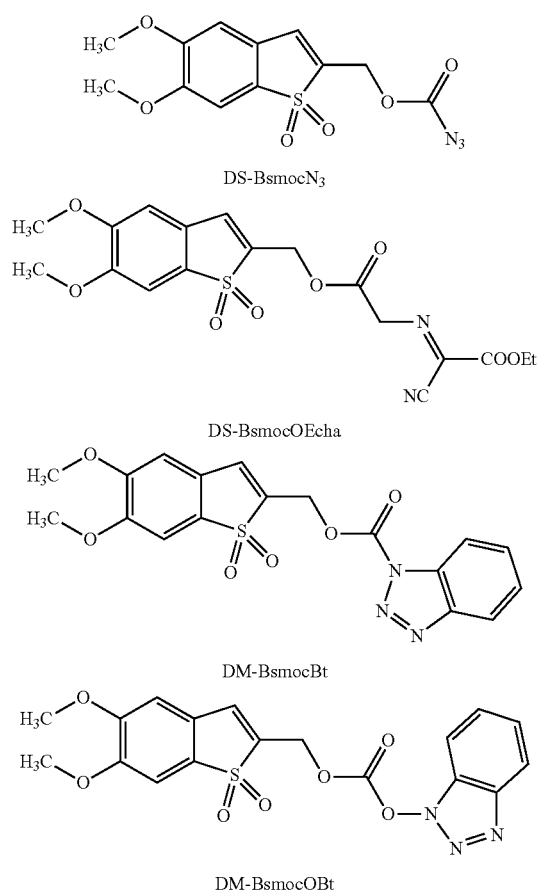

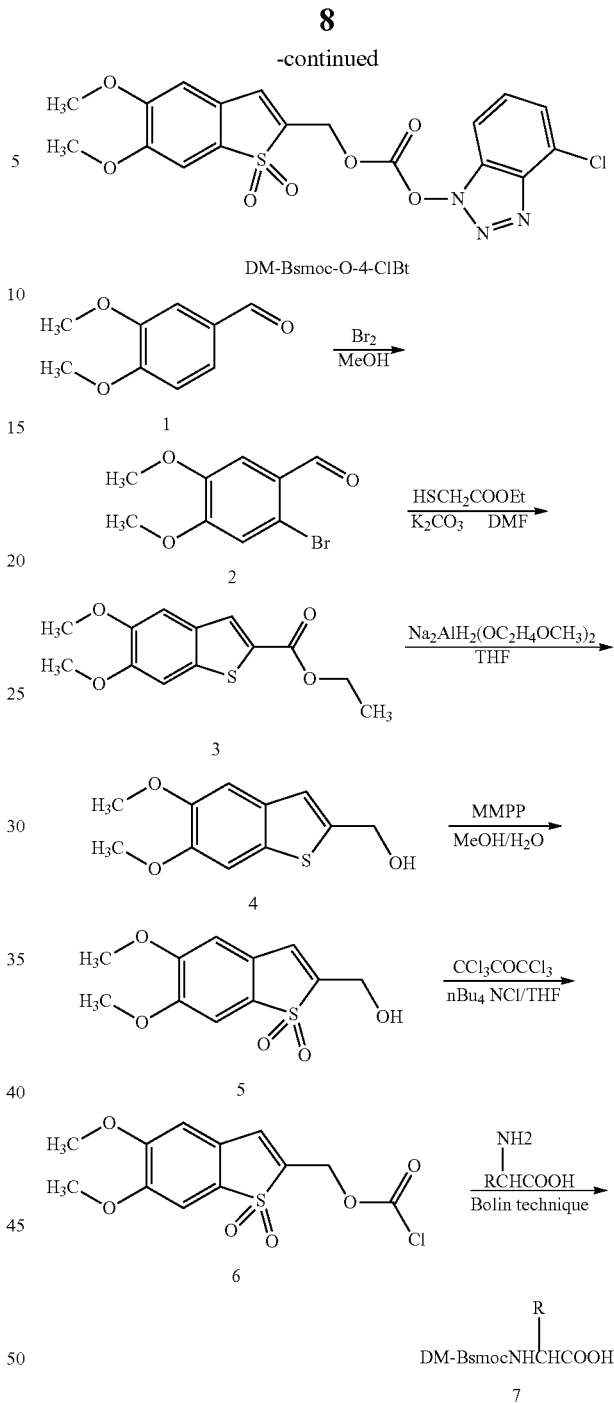

An alternate route to the DM-Bsmoc amino acids begins with the same veratraldehyde 1 which upon treatment with malonic acid in a Knoevenagel-Doebner process gives the cinnamic acid 8 and its cyclization via thionyl chloride to give 3-chloro derivative 9. The extra chlorine atom introduced in this step can be removed by transfer hydrogenolysis via ammonium formate to give 11 which is then converted in the normal manner via reduction with sodium borohydride to 4 followed by oxidation via MMPP to give 5 and then reaction with triphosgene to give 6. Alternatively, complex aluminum- or borohydride reductions of 10 can give the desired 2-methyl alcohol and remove the 3-chloro substituent in the same step.

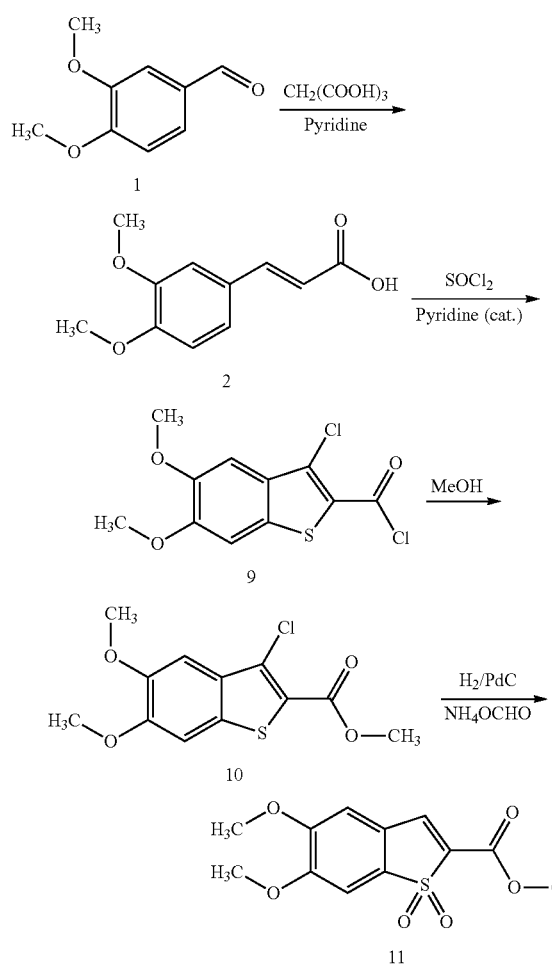

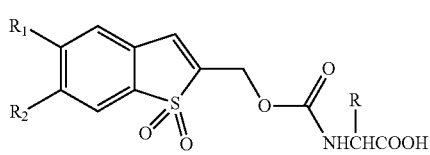

12a $R_1$=MeO, $R_2$=OCH$_2$CH$_2$OMe
12b $R_1$=OCH$_2$CH$_2$OMe, $R_2$=MeO
12c $R_1$=MeO, $R_2$=OCH$_2$SO$_3$K
12d $R_1$=OCH$_2$SO$_3$K, $R_2$=MeO
12e $R_1$=MeSO$_2$, $R_2$=H
12f $R_1$=H, $R_2$=MeSO$_2$
12g $R_1$=$R_2$=MeSO$_2$
12h $R_1$=MeO, $R_2$=MeO(CH$_2$CH$_2$O)n
12i $R_1$=MeO(CH$_2$CH$_2$O)n, $R_2$=MeO
12j $R_1$=Me$_3$N$^+$, $R_2$=H
12k $R_1$=H, $R_2$=Me$_3$N$^+$
12l $R_1$=MeO, $R_2$=MeSO$_2$
12m $R_1$=MeSO$_2$, $R_2$=MeO
12n $R_1$=Cl, $R_2$=H
12o $R_1$=H, $R_2$=Cl
12p $R_1$=Cl, $R_2$=Cl.

wherein Me is a methyl group and R is a functional group of an amino acid.

Increased water solubility may be obtained by adding a 3-alkoxy substituent to the benzo[b]thiophene ring system as in structure 13 wherein $R_1$ and $R_2$ are as depicted in structure 12 (any one of 12a-12m) and $R_3$=MeO—, MeOCH$_2$CH$_2$O—, or MeO(CH$_2$CH$_2$O)$_n$—, and R is a functional group of an amino acid. Such compounds are easily available via the corresponding 3-chloro derivatives such as 10. In addition to methoxy and ethyleneoxy substituents enhanced water solubility can be promoted by the introduction of methylsufonyl substituents whether alone or in combination with an alkoxy substituent.

In addition to the 5,6-dimethoxy substituents which are responsible for the crystallinity and enhanced water solubility of these DM-Bsmoc derivatives, in some embodiments, modifications of these groups can be used to tune their properties for specific purposes. In certain embodiments, the modifications may be used to provide enhanced crystallinity. In other embodiments, the modifications may be used to provide partial or complete water solubility. Enhanced water solubility may be achieved by way of the compounds below. For example, acid 12a would be available readily from vanillin or 12b from isovanillin. The latter would more readily be available at a late stage from selective removal of the methoxy group of acid 12 ($R_1$=$R_2$=MeO) para to the sulfone unit followed by reaction with methoxyethyl bromide. Similarly, highly water soluble sulfonic acid salts 12c and 12d would be available via appropriate chemistry from potassium bromomethanesulfonate.

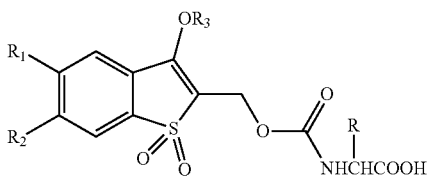

As an electron-withdrawing substituent the MeSO$_2$ group also enhances the stability of the benzo[b]thiophene-2-methyl system toward acidic reagents and in addition enhances the speed of the deblocking step. This can be seen in the case of the N-p-chlorophenylurethane derived from 5-(methylsulfonyl)benzo[b]thiophenesulfone-2-methanol relative to the unsubstituted analog (Bsmoc-NHC$_6$H$_4$—Cl-p) whereby treatment with piperidine in CDCl$_3$ (NMR monitoring) shows the methylsulfonyl derivative to be deblocked about six times more readily. Tables 1A and 1B show the approximate half times for the reaction of substituted Bsmoc p-chloroaniline derivatives with 2 eq of piperidine in CDCl$_3$ according to $^1$H-NMR analysis. A snapshot of the deblocking process is shown in FIG. 1.

Tables 1A and 1B. Approximate half times for the reaction of R-Bsmoc-PCA urethane and piperidine

TABLE 1A

| Substrate | 3-Me-Bsmoc-PCA | 4-Me-Bsmoc-PCA | 5-Me-Bsmoc-PCA | Bsmoc-PCA | 5,6-MeO-Bsmoc-PCA | 5-Ac—NH-Bsmoc-PCA |
|---|---|---|---|---|---|---|
| $t_{1/2}$ 2 eq piperidine in $CDCl_3$ | 360 min | 150 min | 6-7 min | 6-7 min | 3-4 min | 3 min |

TABLE 1B

| Substrate | Bsmoc-PCA | 5-Cl-Bsmoc-PCA | 6-Cl-Bsmoc-PCA | 5-$MeSO_2$-Bsmoc-PCA | 5-$NO_2$-Bsmoc-PCA | 6-$MeSO_2$-Bsmoc-PCA |
|---|---|---|---|---|---|---|
| $t_{1/2}$ 2 eq piperidine in $CDCl_3$ | 6-7 min | 2 min | 2 min | <1 min | <1 min | <1 min |

A particularly favored system would be 12l since the protecting group would be easily available from the inexpensive starting material vanillin. It is interesting that deblocking is faster than for Bsmoc with both electron-donating substituents (5,6-dimethoxy) and electron-withdrawing substituents (5- or 6-methylsufonyl) although to a greater degree with the latter. For the former the effect may be related to inductive electron withdrawal.

Other systems for which an increased rate of deblocking was noted include the 5-nitro and the 5- and 6-chloro-Bsmoc derivatives. Of the systems examined the relative rates are as follows: nitro-Bsmoc≈methanesulfonyl-Bsmoc>chloro-Bsmoc>5,6-dimethoxy-Bsmoc>Bsmoc. Especially favored are the 5- or 6-methanesulfonyl derivatives either as such or substituted with an additional methoxy substitutent. Thus the 5-methoxy-6-methanesulfonyl derivative is easily accessible from inexpensive vanillin via the Newman-Kwart rearrangement (see Example 30), normally a difficult reaction to achieve but in this case occurring at a relatively low temperature in diethylene glycol diethyl ether due to the prresence of the activating aldehyde function. Conversion of the resulting thiol to the S-methyl derivative (see Example 31) followed by cyclization and oxidation gives the appropriate benzo[b]thiophene precursor of the analogous Bsmoc residue.

In view of the increased speed of the deblocking process for the 5-methansulfonyl-protected amino acids it may be reasonable to foresee difficulties due to premature deblocking with such systems. Two tests for the possible incursion of the premature deblocking during the use of the 5-$MeSO_2$-Bsmoc residue were carried out. The first involved the coupling of 5-$MeSO_2$-Bsmoc-Gly-F to glycine ethyl ester. HPLC showed no traces of the by-product expected due to preliminary deblocking but only the expected dipeptide. A second test involved the solid phase assembly of the sequence 14

14
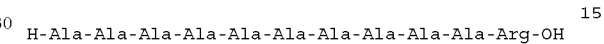
H-Leu-Thr-Gly-Lys-Ser-Leu-Glu-Ala-Asp-Gly-$NH_2$ which was carried out according to Bayer (Henkel, B.; Bayer, E. *J. Pept. Sci.*, 2001, 7, 152) who demonstrated double incorporation of leucine via premature deblocking during the use of the 2-nitro-Fmoc protecting group. For 14 two syntheses were performed one via Bsmoc chemistry completely and the other via Bsmoc chemistry up to the last amino acid which was incorporated via 5-$MeSO_2$-Bsmoc-Leu-OH. In contrast to Bayer's results neither synthesis showed more than traces (<0.5%) of the undecapeptide bearing an extra leucine unit. Similar results are expected for the 5-methoxy-6-methansulfonyl-Bsmoc derivatives.

The deblocking superiority of the 5-$MeSO_2$-Bsmoc residue for solid phase synthesis is shown by the assembly of the notoriously difficult [Larsen, B. D.; Holm, A. *Int. J. Pept. Prot, Res.* 43, 1, (1994)] deca-alanine sequence 15, here built onto arginine 15
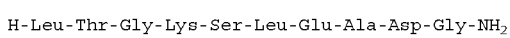
H-Ala-Ala-Ala-Ala-Ala-Ala-Ala-Ala-Ala-Ala-Arg-OH For more facile analysis. Assembly via 5-$MeSO_2$-Bsmoc chemistry gave the target peptide as the major product along with some of the deletion peptides but no peptides containing any undeblocked 5-$MeSO_2$-Bsmoc residues whereas under the same conditions (single deblocking for 4 min) Bsmoc chemistry gave none of the desired peptide but significant amounts of undeblocked Bsmoc-protected peptides. The latter result is similar to what is observed with Fmoc chemistry.

Amino acids that may be used with the present disclosure may include arginine (Arg), histidine (His), lysine (Lys), aspartic acid (Asp), glutamic acid (Glu), serine (Ser), threonine (Thr), asparagine (Asn), glutamine (Gln), cysteine (Cys), glycine (Gly), proline (Pro), alanine (Ala), isoleucine (Ile), leucine (Leu), methionine (Met), phenylalanine (Phe), tryptophan (Trp), tyrosine (Tyr), valine (Val), and related compounds. The appended Table 2 shows the 20 proteinogenic amino acids, indicating the portion that is the functional group. The α-protected amino acids of the embodiments described may also comprise amino acids such as selenocysteine(Sec), pyrrolysine (Pyl) and hydroxyproline (Hyp).

Other α-protected molecules of the embodiments described may comprise non-natural amino acids, non-proteinogenic amino acids or related compounds, or any amino acid or other compound having a free primary or secondary amine group.

The DM-Bsmoc described in the present disclosure may be used as a protecting group for modified amino acid derivatives. This may include N-methyl amino acids (methylated peptides), phosphoamino acids (phosphopeptides), and glycosylated-amino acids (glycopeptides). Phosphoamino acids may include phosphoserine, phosphotyrosine, and phosphothreonine.

In certain embodiments, the DM-Bsmoc described in the present disclosure may be used as a protecting group for peptidomimetics. Peptidomimetics may include small protein-like chains designed to mimic a peptide. They may be non-natural versions of peptides that may be constructed by solid phase synthesis similar to natural peptides. They may use different building blocks which contain an amino group that may be protected with the DM-Bsmoc residue.

The following table (Table 2) includes the monomers for natural peptides and peptidomimetics

TABLE 2

| Peptidomimetic | Monomer |
|---|---|
| Natural Peptide | |
| Azapeptides | |
| β-peptide | β² |
| | β³ |
| Peptoid | |
| Peptide Nucleic Acid (PNA) | |

Wherein R' may be a functional group.

The DM-Bsmoc described in the present disclosure may also be used in the synthesis of depsipeptides including the various depsidipeptide building blocks. A depsipeptide may be a peptide in which one or more of its amide groups is replace by the corresponding ester. These may allow for the introduction of depsipeptide units at any point in a peptide chain involving an amino acid such as serine, threonine, and cysteine. The depsidipeptide from DM-Bsmoc-Ala-OH and Boc-Thr-OH structure is shown below.

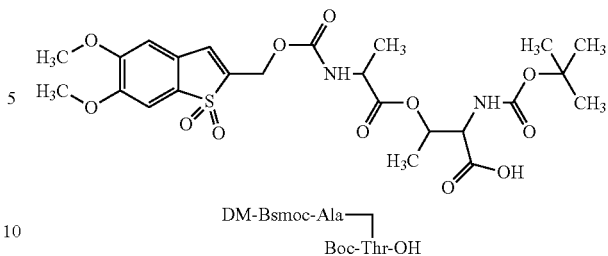

DM-Bsmoc-Ala—⏋
Boc-Thr-OH

The DM-Bsmoc described in the present disclosure may also be used in the synthesis of pseudo-proline dipeptides which may allow protection of the pseudo-proline dipeptide building blocks involving serine, threonine, and cysteine. The pseudo-proline dipeptide from DM-Bsmoc-Ala-OH and a threonine-based pseudo-proline is shown below. In some instances, DM-Bsmoc may be referred to as Dmoc.

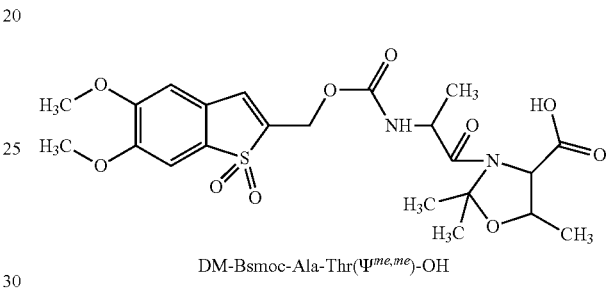

DM-Bsmoc-Ala(Ψ$^{me,me}$)-OH

EXAMPLE 1

Preparation of 2-Bromo-4,5-dimethoxybenzaldehyde

In a 5 liter (L) 3-neck round bottomed flask fitted with a mechanical stirrer, a dropping funnel and a thermometer, there was added 500 grams (g) (3001 millimoles (mmol)) of veratraldehyde in 1500 milliliter (mL) of methanol. Due to the endothermic solution process the temperature of the solution dropped below 25° C. and therefore the solution was warmed with a heating mantle until the temperature again reached 25° C. At this point 573.5 g (3589 mmol, 185 mL) of bromine was added dropwise at such a rate that the temperature remained under 40° C. to avoid the formation of the 2,3-dibromo derivative. The addition required about one hour and gave a reddish yellow solution. After about two hours a precipitate began to separate and after three hours, 7 L of water was added and the precipitate was filtered and washed with an additional 7 L of water. Recrystallization from 7 L of ethanol gave 600 g (81.3%) of the bromo aldehyde, melting point (m. p.) 145-146° C. (lit. m.p. 149-151° C., as shown in S. Chandrasekhar et al. *Tetrahedron* 62, 12908 (2006)); IR (NaCl): 1683, 1594, 1504 cm$^{-1}$; $^1$H-NMR (CDCl$_3$) δ 3.88 (s, 3), 3.93 (s, 3), 7.02 (s, 1), 7.37 (s, 1), 10.14 (s, 1). $^{13}$C-NMR (CDCl$_3$, 75 MHz): δ 56.05, 56.44, 110.28, 115.34, 120.26, 126.41, 148.76, 154.37, 190.55.

EXAMPLE 2

Preparation of Ethyl 5,6-dimethoxybenzo[b]thiophene-2-carboxylate

In a 5 L 3-neck round bottomed flask fitted with a mechanical stirrer, a condenser and a blanket of nitrogen, was placed a mixture of 2000 mL of DMF, 500 g (2040.3 mmol) of 2-bromoveratraldhyde, 385 g (2799 mmol) of $K_2CO_3$, 10 g (52.5 mmol) of CuI, 5.5 mL (52.5 mmol) of diethylamine and 285 g (2371.6 mmol, 260 mL) of ethyl mercaptoacetate. The mixture was stirred vigorously and the temperature was raised to 105° C. with a heating mantle. The temperature was maintained at this point (range 105-110° C.) for 24 hours. A sample taken after five hours showed that at that time the reaction was nearly complete (about 98% complete). The mixture was cooled to room temperature and filtered to remove inorganic salts and the filtrate was evaporated to remove all of the DMF. The inorganic precipitate was washed with 900 mL of ethyl acetate and this solution set aside. The residue from the evaporation of DMF was redissolved in 1600 mL of ethyl acetate (EtOAc) and mixed with the 900 mL of EtOAc set aside and the whole washed with three 400-mL portions of water to which sodium chloride or 1N HCl may be added to help separate the layers. The combined organic solvent was dried over $MgSO_4$ and evaporated to dryness to give 512 g (94.2%) of the ester as a faint brown or reddish brown solid. The crude product was used as such in the next step although upon recrystallization from ethanol it gave 300 g (55%) of the pure ester, m. p. 76-77° C. (lit. m. p. 82-84° C., as shown in Hui-Fang Guo et al. *J. Med. Chem.* 53, 1819 (2010)); IR (NaCl): 1705, 1517, 1235 cm$^{-1}$; $^1$H-NMR (CDCl$_3$) δ 1.38 (t, 3), 3.92 (s, 3), 3.94 (s, 3) 4.35 (q, 2), 7.20, (s, 1), 7.21 (s, 1), 7.90 (s, 1). $^{13}$C-NMR (CDCl$_3$, 75 MHz): δ14.30, 55.91, 56.03, 61.22, 103.31, 105.52, 130.02, 131.37, 132.23, 135.96, 148.61, 150.43, 162.76.

EXAMPLE 3

Preparation of 5,6-Dimethoxybenzo[b]thiophene-2-methanol

In a 5 L 3-neck round bottomed flask fitted with a mechanical stirrer and a condenser was placed 512 g (1923 mmol) of crude ethyl 5,6-dimethoxybenzo[b]thiophene-2-carboxylate and 1500 mL of THF. The solution was stirred and cooled in an ice bath and 1110 g (3846 mmol) of Vitride solution (70% in toluene) was added dropwise at 0-5° C. over a period of about 50 minutes. After addition was complete, the reaction mixture was stirred in the ice bath for an additional 15 minutes and then treated dropwise with 1200 mL of water during which effervescence ceased and the stirrer stopped due to the formation of a hard cake. The solvent was poured off and the residual cake was washed with an additional 200 mL of tetrahydrofuran (THF) and the combined organic layers were dried over $MgSO_4$ and rotavaped off to give about 398.0 g of the crude sulfide alcohol as a black colored solid.

The crude solid could be used as such in the next step. For purification a 50-g sample was dissolved in hot ethanol and precipitated with water to give 33 g (56%) of the purified sulfide alcohol as a tan colored solid, m. p. 95-96° C. (lit. m.p. 108-110° C., as shown in C. D. Sferdean, Ph. D. thesis. University of Massachusetts Amherst, Mass. (2006)); IR (DCM): 1606, 1534, 1482, 1153 cm$^{-1}$; $^1$H-NMR (CDCl$_3$) δ 1.89 (br s, 1), 3.93 (s, 3), 3.94 (s, 3) 4.87 (d, 2), 7.09, (s, 1), 7.14 (s, 1), 7.24 (s, 1). $^{13}$C-NMR (CDCl3, 75 MHz): δ 55.92, 56.02, 103.95, 104.78, 121.56, 132.56, 132.88, 142.80, 147.95, 147.97.

EXAMPLE 4

Preparation of 5,6-Dimethoxybenzo[b]thiophenesulfone-2-methyl Alcohol (A) Oxidation via MMPP To a stirred solution of 70 g (312.1 mmol) of the crude sulfide alcohol in 350 mL of methanol at 0° C. was added portionwise 210 g (424.5 mmol) of monoperoxyphthalic acid magnesium salt hexahydrate (Aldrich Chemical Co.) with 70 mL of water also added slowly over the same period of time. After the addition was complete the reaction mixture was stirred at room temperature for 20 minutes. The yellow precipitate was filtered, washed with water and EtOAc to give 54.3 g (67.8%) of the sulfone alcohol, m. p. 175-177° C. dec (lit. m. p. 199-200° C. as shown in C. D. Sferdean, Ph. D. thesis, University of Massachusetts, Amherst, Mass. (2006)); IR (NaCl): 1585, 1495, 1307, 1136 cm$^{-1}$; $^1$H-NMR (DMSO-d$_6$) δ 3.84 (s, 6), 4.40 (dd, 2), 5.60 (t, 1), 7.17, (s, 1), 7.22 (s, 1), 7.47 (s, 1). $^{13}$C-NMR (DMSO, d$_6$, 75 MHz): δ 54.03, 56.07, 56.45, 105.03, 108.41, 124.11, 126.01, 128.60, 143.81, 149.97, 152.78.

(B) Oxidation via $H_2O_2$

In a 5-L 3 neck round bottomed flask fitted with a condenser, a thermometer and a mechanical stirrer, there was placed 300 g (1337.7 mmol) of the crude sulphide alcohol, 0.46 g (1.4 mmol) of sodium tungstate dihydrate, 0.23 g (1.4 mmol) of phenylphosphonic acid and 300 mL of methanol. There was added 1200 ml of $H_2O_2$ (30%) portionwise at such a rate that the temperature did not exceed 40° C. The reaction temperature remained at 40° C. for about 5 hours and then the mixture was left at room temperature over night. A yellow precipitate began to come out and accumulated over time. Filtration gave 162.4 g (50%) of the sulfone alcohol as a yellow solid, m. p. 181-183° C. dec. The proton NMR agreed with that of the sample obtained by method A.

EXAMPLE 5

Preparation of 5,6-Dimethoxybenzo[b]thiophenesulfone-2-methyl chloroformate

In a 1 L 3-neck round bottomed flask fitted with a condenser, thermometer, stopcock and a magnetic stirrer under an atmosphere of nitrogen, was added 70 g (273.2 mmol) of 5,6-dimethoxybenzo[b]thiophenesulphone-2-methanol, 45.5 g (153.3 mmol) of triphosgene, 1.0 g (3.6 mmol) of tetra-n-butylammonium chloride and 250 ml of THF (Pharmco Aaper, HPLC grade). The reaction mixture was stirred for a period of 5 hours in a cold tap water bath to which ice could be added at the beginning so that the temperature of the reaction mixture never exceeded 25° C. Infrared examination showed that after 5 hours the sulfone alcohol was no longer visible. There was added 250 ml of cold ether and the reaction mixture was filtered to give 77.3 g (88.7%) of highly pure chloroformate as a yellow solid. An analytical sample was obtained by recrystallization from THF at −20° C. overnight, m.p. 171-173° C. dec., IR (NaCl): 1777, 1307, 1141 cm$^{-1}$; $^1$H-NMR (CDCl$_3$) δ 3.95 (s, 3), 3.96 (s, 3) 5.23 (d, 2), 6.86 (s, 1), 7.16 (d, 1), 7.23 (s, 1). $^{13}$C-NMR (CDCl$_3$, 75 MHz): δ 56.57, 56.6762.21, 104.72, 108.18, 123.06, 128.92, 132.48, 135.52, 150.94, 151.58, 153.29; Anal. Calcd for $C_{12}H_{11}ClO_6S$: C, 45.22; H, 3.48. Found: C, 45.23; H, 3.10. $^1$H-NMR examination of the crude chloroformate showed the presence of approximately 1.0% of unreacted sulfone alcohol and 0.25% of 5,6-dimethoxybenzo[b]thiophenesulfone-2-methyl chloride. The crude product was used as such in the synthesis of the DM-Bsmoc amino acids by the Bolin technique.

EXAMPLE 6

Preparation of 5,6-Dimethoxybenzo[b]thiophenesulfone-2-methyl N-succinimidyl Carbonate To a solution of 21.65 g (188.3 mmol) of N-hydroxysuccinimide and 15.82 g (188.3 mmol) of NaHCO$_3$ in 150 ml of water was added 150 ml of MeCN followed by 50 g (156.9 mmol) of 5,6 dimethoxybenzo[b]thiophenesulfone-2-methyl chloroformate. The reaction mixture was stirred for 15 minutes. An IR sample showed that the reaction was complete after 5 min. The mixture was filtered and dried in air to give 53.2 g (85.3%) of the carbonate. An analytical sample was obtained by trituration twice with hot hexane, m. p. 242-245° C. dec.; IR (NaCl): 1816, 1790, 1747, 1307, 1217, 1136 cm$^{-1}$; $^1$H-NMR (CDCl$_3$+TFA) δ 2.97 (s, 4), 3.97 (d, 6), 5.31 (d, 2) 6.95 (s, 1), 7.28 (s, 1), 7.35 (s, 1). $^{13}$C-NMR (DMSO, d$_6$, 75 MHz): δ 25.51, 56.15, 56.4, 66.18, 105.25, 109.19, 123.07, 124.24, 127.97, 131.16, 134.69, 135.96, 151.04, 152.83, 171.89, 172.25. Anal. Calcd for C$_{16}$H$_{15}$NO$_9$S: C, 48.36.79; H, 3.80; N, 3.52. Found: C, 47.88; H, 3.82; N, 3.50.

EXAMPLE 7

Preparation of 3,4-Dimethoxycinnamic Acid

In a 1 L round bottomed flask fitted with a magnetic stirrer and a reflux condenser, a mixture of 166 g (1 mol) of veratraldehyde and 208 g (2 mol) of malonic acid in 500 mL of pyridine and 5 mL of piperidine was refluxed for 4 h. The excess pyridine was evaporated using a rotavap and 3 L of water was added to the syrupy residue which caused the formation of a solid. The mixture was acidified with 250 mL of concentrated HCl with stirring. Filtration and washing with three 100-mL portions of water and drying in air afforded 150 g (71.4%) of the cinnamic acid, m.p. 183-185° C. (lit. m.p. 180-182° C.) as shown in J. G. Stuart et al, *J. Het. Chem.*, 24. 1589 (1987); $^1$H-NMR (DMSO-d$_6$) δ 3.78 (s, 3), 3.80 (s, 3), 6.44 (d, 1), 6.96 (d, 1) 7.19 (dd, 1), 7.31 (d, 1), 7.52 (d, 1).

EXAMPLE 8

Preparation of Methyl 3-chloro-5,6-dimethoxybenzo [b]thiophene-2-carboxylate Into a 2 L round bottomed flask fitted with a magnetic stirrer and a reflux condenser, a suspension of 100 g (475 mmol) of 3,4-dimethoxycinnamic acid in 750 mL of chlorobenzene was treated with 150 mL (2000 mmol) of thionyl chloride. The suspension was stirred at room temperature and, after 30 minutes, 10 mL of pyridine was added. The reaction mixture was refluxed for 24 hours with stirring. The resultant solid was filtered and re-dissolved in 1.5 L of methanol. The reaction mixture was refluxed again for 24 hours and then cooled. The solid was filtered, washed with methanol and dried under vacuum to give 61.3 g (45%) of the ester as a brownish-yellow solid, m.p. 212-214° C. (lit. m.p. 215-216° C., as shown in C. M. Bonnin et al, *Aust. J. Chem.*, 32, 833 (1979)); $^1$H-NMR (DMSO-d$_6$) δ 3.87 (s, 3), 3.88 (s, 3), 3.89 (s, 3), 7.28 (s, 1), 7.68 (s, 1).

EXAMPLE 9

Preparation of Methyl 5,6-dimethoxybenzo[b]thiophene-2-carboxylate

Into a 100-mL round-bottomed flask containing 30 mL of methanol cooled in an ice bath, 100 mg of 10% Pd-on-carbon catalyst (Aldrich) was added. The mixture was stirred at room temperature and 100 mg of palladium acetate followed by 300 mg of ammonium formate was added. A flocky suspension with a clear supernatant layer results and 140 mg (0.49 mmol) of methyl 3-chloro-5,6-dimethoxybenzo[b]thiophene-2-carboxylate was added and the mixture stirred at room temperature for 24 hours. The mixture was filtered into an evaporating dish with washing on the filter paper with several sprays of methanol. As the methanol evaporates in the hood a flocky white material separates at first. When the methanol has all evaporated, about 15 mL of water is added, the mixture stirred well, and the white flaky solid filtered and dried in air to give 100 mg (81.2%) of the de-chlorinated methyl ester, mp. 155-158° C. (lit. m.p. 158-159° C. as shown in T. R. Beck, *J. Org. Chem.*, 37, 3224 (1972), $^1$H-NMR (CDCl$_3$); δ 3.92 (s, 3) 3.95 (s, 3), 3.97 (s, 3), 7.24 (s, 1), 7.25 (s, 1) 7.94 (s, 1).

EXAMPLE 10

General Procedure for the Preparation of 5,6-Dimethoxy-1,1-dioxobenzo[b]thiophene-2-methoxycarbonyl Amino Acids Using the Bolin Technique To a suspension of 39.02 mmol of an amino acid in 120 mL of dry DCM, was added in one portion 9.3 mL (78.04 mmol) of chlorotrimethylsilane followed by the dropwise addition of 13.6 mL of diisopropylethylamine under a N$_2$ atmosphere. The reaction mixture was refluxed for 2 hours. Crude 5,6-DM-BsmocCl (12.43 g, 39.02 mmol) was added at once followed by 30 ml of DCM. The reaction mixture was allowed to stand at RT overnight. The solvent was removed in vacuo and the resulting oil was dissolved or suspended in 120 mL of 5% NaHCO$_3$ solution and extracted with DCM or ethyl acetate (3×40 ml). The aqueous layers were acidified to pH 2 with concentrated HCl and extracted with EtOAc (3×50 mL). The extracts were combined and washed with saturated NaCl solution (2×40 mL), dried over MgSO$_4$, filtered and the solvent was evaporated in vacuo to give the solid amino acids, the properties of which are given below.

5,6-DM-Bsmoc-Asp(OtBu)-OH

Evaporation of ethyl acetate gave 10 g (54.3%) of the acid as a yellow amorphous solid, m.p. 65-75° C.; IR (NaCl): 1136, 1303 (SO2), 1730 (CO, acid; urethane) cm$^{-1}$; $^1$H-NMR (CDCl$_3$) δ 1.42 (s, 9), 2.85 (dq, 2), 3.93 (d, 6), 4.61 (distorted pentet, 1), 5.01 (distorted d, 2), 5.97 (distorted d, 1) 6.82 (s, 1), 7.06 (s, 1) 7.2 (s, 1). $^{13}$C-NMR (CDCl3, 75 MHz): δ27.94, 37.46, 50.47, 56.40, 56.43, 82.24, 104.44, 107.97, 123.70, 128.64, 130.13, 13038, 138.02, 150.80, 153.03, 155.50, 170.065, 174.94. HRMS: [M+Na]$^+$ calcd for C$_{20}$H$_{25}$NO$_{10}$S: 494.1091; obsd: 494.1077

5,6-DM-Bsmoc-Glu(OtBu)-OH

Evaporation of ethyl acetate gave 6.8 g (35.9%) of the acid as a yellow amorphous solid, m.p. 60-112° C.; IR (NaCl): 1136, 1303 (SO$_2$), 1730 (CO, acid; urethane) cm$^{-1}$; $^1$H-NMR (CDCl$_3$) δ 1.41 (s, 9), 1.97-2.17 (m, 2), 2.38 (m, 2), 3.91 (d, 6), 4.35 (distorted pentet, 1), 5.04 (distorted d, 2), 5.86-6.07 (distorted d, 1) 6.81 (s, 1), 7.04 (s, 1) 7.17 (s, 1). $^{13}$C-NMR (CDCl3, 75 MHz): δ27.23, 28.11, 31.62, 53.57, 56.53, 56.58, 57.04, 81.37, 104.59, 108.03, 123.82, 128.81, 130.21, 138.21, 150.95, 153.16, 155.65, 172.60, 175.54. HRMS: [M+Na]$^+$ calcd for C$_{21}$H$_{27}$NO$_{10}$S: 508.1248; obsd: 508.1225

5,6-DM-Bsmoc-Lys(Boc)-OH

Evaporation of ethyl acetate gave 10 g (48.5%) of the acid as a yellow amorphous solid, m.p. gas evolution at 80-100° C. with melting at 130° C.; IR (NaCl): 1136, 1307 ($SO_2$), 1722 (CO, acid; urethane) $cm^{-1}$; $^1$H-NMR ($CDCl_3$) δ 1.40-1.86 (m, 15), 3.08 (m, 2), 3.91 (d, 6), 4.32 (m, 1), 5.01 (m, 2), 5.94 to 6.32 (m, 1) 6.81 (s, 1), 7.04 (s, 1) 7.16 (s, 1), 9.03 (bs, 1). $^{13}$C-NMR ($CDCl_3$, 75 MHz): δ 22.43, 28.39, 29.46, 31.57, 40.12, 41.11, 53.95, 56.41, 56.46, 56.81, 104.37, 108.01, 123.75, 128.60, 130.01, 138.19, 150.74, 153.01, 155.61, 156.44, 158.24, 175.44. Anal. Calcd for $C_{23}H_{32}NO_{10}S$: C, 52.26; H, 6.10; N: 5.30. Found: C, 52.03; H, 5.99; N, 5.12.

5,6-DM-Bsmoc-Ser(tBu)-OH

Evaporation of ethyl acetate gave 6 g (34.7%) of the acid as a yellow amorphous solid, m.p. gas evolution at 80-100° C. with melting at 130° C.; IR (NaCl): 1136, 1303 ($SO_2$), 1730 (CO, acid; urethane), $cm^{-1}$; $^1$H-NMR ($CDCl_3$) δ 1.11 (s, 9), 3.56 (dd, 1), 3.83 (dd, 1), 3.85 (d, 6), 4.42 (distorted pentet, 1), 5.01 (distorted d, 2), 5.86 (distorted d, 1) 6.79 (s, 1), 7.04 (s, 1) 7.16 (s, 1). $^{13}$C-NMR ($CDCl_3$, $d_6$, 75 MHz): δ 27.20, 54.48, 56.40, 56.82, 61.57, 76.84, 104.44, 107.93, 123.72, 128.64, 130.10, 138.12, 150.78, 153.02, 155.61, 174.43. HRMS: $[M+Na]^+$ calcd for $C_{19}H_{25}NO_9S$: 466.1142; obsd: 466.1119.

5,6-DM-Bsmoc-Ala-OH

Evaporation of ethyl acetate gave 13.0 g of the crude product which was recrystallized from hot water to give 11.74 g (81.7%) of the acid as an off white solid, m.p. 194-195° C.; IR (NaCl): 1136, 1303 ($SO_2$), 1730 (CO, acid; urethane) $cm^{-1}$; $^1$H-NMR ($CDCl_3$) δ 1.35 (d, 9), 3.86 (d, 6), 4.2 (pentet, 1), 4.95 (q, 2), 5.57 and 5.84 (two d, 1) 6.77 (s, 1), 7.00 (s, 1) 7.13 (s, 1). $^{13}$C-NMR (DMSO, $d_6$, 75 MHz): δ 17.06, 49.40, 55.71, 56.15, 56.44105.16, 108.90, 123.32, 128.28, 130.56, 138.05, 150.62, 152.82, 155.27, 174.27. Anal. Calcd for $C_{15}H_{17}NO_8S$: C, 48.51; H, 4.61; N: 3.77. Found: C, 48.69; H, 4.58; N: 3.70.

5,6-DM-Bsmoc-Phe-OH

Evaporation of ethyl acetate gave 13.8 g (79%) of the acid as an off white amorphous solid, m.p 95-105° C.; IR (NaCl): 1136, 1303 ($SO_2$), 1730 (CO, acid; urethane) $cm^{-1}$; $^1$H-NMR ($CDCl_3$) δ 2.98 (dd, 1), 3.14 (dd, 1), 3.88 (d, 6), 4.61 (q, 1), 5.01 (distorted q, 2), 5.59 and 5.97 (two d, 1) 6.76 (distorted d, 1), 6.93 (distorted d, 1) 7.2 (m, 6). $^{13}$C-NMR (DMSO, $d_6$, 75 MHz): δ 36.46, 55.74, 56.15, 56.44, 105.18, 108.83123.30, 126.46, 128.27, 129.16, 130.50, 137.93, 138.00, 150.64, 152.81, 155.47, 173.23. Anal. Calcd for $C_{21}H_{21}NO_8S$: C, 56.37; H, 4.73; N: 3.13. Found: C, 56.21; H, 4.80; N, 3.04.

5,6-DM-Bsmoc-Thr(tBu)-OH

Evaporation of ethyl acetate gave 14 g of the crude acid as a yellow amorphous solid which was recrystallized from hot EtOH to give 10.7 g (60.%) as an off white solid, m.p. 178-179° C.; IR (NaCl): 1136, 1303 ($SO_2$), 1730 (CO, acid; urethane) $cm^{-1}$; $^1$H-NMR ($CDCl_3$) δ 1.15 (d, 3), 1.23 (s, 9), 3.92 (d, 6), 4.2 (m, 2), 5.10 (distorted q, 2), 5.65 and 5.8 (two d, 1) 6.81 (s, 1), 7.01 (s, 1) 7.20 (s, 1). $^{13}$C-NMR ($CDCl_3$, 75 MHz): δ 19.03, 28.03, 56.49, 56.54, 57.02, 59.06, 66.80, 75.93104.60, 107.87, 108.05, 123.76, 128.87, 129.75, 138.35, 150.91, 153.12, 155.69, 173.36. Anal. Calcd for $C_{20}H_{27}NO_9S$: C, 52.51; H, 5.95; N: 3.06. Found: C, 52.70; H, 6.01; N, 2.96.

5,6-DM-Bsmoc-Tyr(tBu)-OH

Evaporation of ethyl acetate gave 11.3 g (55.7%) of the crude acid as a yellow amorphous solid, m.p: softens at 90° C. and melts at 140 to 155° C.; IR (NaCl): 1136, 1303 ($SO_2$), 1730 (CO, acid; urethane) $cm^{-1}$; $^1$H-NMR ($CDCl_3$) δ 1.30 (s, 9), 3.04 (dd, 1), 3.14 (dd, 1), 3.91 (d, 6), 4.6 (q, 1), 4.97 (distorted q, 2), 5.43 and 5.65 (two d, 1) 6.80 (s, 1), 6.89 (d, 2), 6.97 (m, 1), 7.06 (d, 2) 7.20 (s, 1). $^{13}$C-NMR ($CDCl_3$, 75 MHz): δ 28.83, 37.08, 55.01, 56.48, 56.87, 77.48, 104.50, 108.04, 123.72, 124.72, 128.66, 129.86, 130.27, 130.65, 137.53, 150.88, 153.09, 154.28, 155.34, 174.91, 175.06. Anal. Calcd for $C_{25}H_{29}NO_9S$: C, 57.79; H, 5.63; N: 2.70. Found: C, 57.47; H, 5.62; N, 2.59.

5,6-DM-Bsmoc-Ile-OH

Evaporation of ethyl acetate gave 14.5 g (90%) of the acid as a yellow amorphous solid, m.p. 85-140° C.; $^1$H NMR ($CDCl_3$): δ 0.86 (t, 3), 0.91 (d, 3), 1.14 (m, 1), 1.42 (m, 1), 1.88 (m, 1), 3.87 (d, 6), 4.28 (dd, 1), 5.01 (dd, 2), 6.78 (s, 1), 7.02 (s, 1), 7.13 (s, 1). HRMS: $[M]^+$ calcd for $C_{18}H_{23}NO_8S$: 413.1144; obsd: 413.1165.

5,6-DM-Bsmoc-Pro-OH

Evaporation of ethyl acetate gave 12.7 g (82%) of the acid as a yellow amorphous solid, m.p. 90-155° C.; $^1$H NMR ($CDCl_3$): δ 1.88 (m, 2), 2.07 (m, 1), 2.19 (m, 1), 3.51 (m, 2), 3.89 (d, 6), 4.38 (dq, 1), 5.08 (distorted q, 2), 6.80 (d, 1), 7.03 (d, 1), 7.13 (d, 1). HRMS: $[M]^+$ calcd for $C_{17}H_{19}NO_8S$: 397.0831; obsd: 397.0847.

5,6-DM-Bsmoc-Trp-OH

Evaporation of ethyl acetate gave 14.4 g (76%) of the acid as a yellow amorphous solid, m.p. 135-203° C.; $^1$H NMR ($CDCl_3$): δ 3.01 (distorted q, 1), 3.18 (dd, 1), 3.86 (s, 6), 4.23 (distorted sextet, 1), 4.9 (distorted q, 2), 6.96-7.55 (m, 8), 7.78 (d, 1, NH), 10.84 (s, 1, NH). HRMS: $[M]^+$ calcd for $C_{23}H_{22}N_2O_8S$: 486.1097; obsd: 486.1098.

5,6-DM-Bsmoc-Cys(Trt)-OH

In this case the work-up was modified by using triethylamine in place of $NaHCO_3$ solution to dissolve the crude amino acid. Thus to the crude acid suspended in 150 mL of water the triethylamine was added until the pH reached 11. The aqueous solution was extracted with 20 mL of DCM and then 2N hydrochloric acid was added until the pH reached 2. Extraction with EtOAc was carried out as described in the general procedure. Evaporation of ethyl acetate gave 11.3 g (45%) of the acid as a yellow amorphous solid, m.p. 128-200° C.; $^1$H NMR (DMSO-$d_6$): δ 2.41 (dd, 1), 2.58 (distorted q, 1), 3.83 (s, 3), 3.85 (m, 1), 3.87 (s, 3), 4.96 (distorted d, 2), 7.21-7.33 (m, 16+), 7.40 (s, 1), 7.54 (s, 1), 7.88 (d, 1, NH). Anal. Calcd for $C_{34}H_{31}NO_8S_2$: C, 63.24; H, 4.84; N: 2.17. Found: C, 62.82; H, 4.67; N, 2.15.

5,6-DM-Bsmoc-Gly-OH

Evaporation of ethyl acetate and then recrystallization from ethanol/water gave 10.3 g (73.9%) of the acid as a white solid, m.p. 210-212° C.; $^1$H NMR (DMSO-d$_6$): δ 3.67 (d, 2), 3.86 (d, 6), 4.97 (s, 2), 7.27 (s, 1), 7.39 (s, 1), 7.53 (s, 1), 7.72 (t, 1). Anal. Calcd for C$_{14}$H$_{15}$NO$_8$S: C, 47.06; H, 4.23; N: 3.92. Found: C, 46.85; H, 4.11; N, 3.73.

5,6-DM-Bsmoc-Val-OH

Evaporation of ethyl acetate and then recrystallization from ethanol/water gave 12.64 g (81.1%) of the acid as a light yellow solid, m.p. 108-110° C.; $^1$H NMR (DMSO-d$_6$): δ 0.89 (t, 6), 2.05 (m, 1), 3.87 (d, 7), 4.97 (q, 2), 7.27 (s, 1), 7.38 (s, 1), 7.53 (s, 1),7.66 (d, 1). Anal. Calcd for C$_{17}$H$_{21}$NO$_8$S: C, 51.12; H, 5.30; N: 3.51. Found: C, 50.86; H, 5.10; N, 3.44.

5,6-DM-Bsmoc-Met-OH

Evaporation of ethyl acetate and then recrystallization from ethanol/water gave 8.4 g (50.0%) of the acid as a light yellow solid, m.p. 73-75° C.; $^1$H NMR (DMSO-d$_6$): δ 1.86-1.94 (m, 2), 2.03 (s, 3), 3.86 (d, 6), 4.10 (distorted sextet, 1), 4.97 (q, 2), 7.26 (s, 1), 7.39 (s, 1), 7.53 (s, 1), 7.79 (d, 1). Anal. Calcd for C$_{17}$H$_{21}$NO$_8$S$_2$.1/2 H$_2$O: C, 46.35; H, 5.03; N: 3.18. Found: C, 46.68; H, 4.85; N, 3.13.

EXAMPLE 11

General Procedure for the Preparation of 5,6-Dimethoxy-1,1-dioxobenzo[b]thiophene-2-methoxycarbonyl Amino Acids Using Dmoc-OSu in Acetonitrile-Water in the Presence of Triethylamine. Method A To a suspension of 39.02 mmol of an amino acid in 400 mL of acetonitrile/water (1/1) was added an amount of triethylamine to give an apparent pH of 9 (approximately 12 mL). The suspension became clear. The pH was kept at 8.5-9.0, after the addition of 5,6-DM-Bsmoc-OSu (15.5 g, 39.02 mmol), by adding triethylamine. The uptake of base ceased after about 15 min after which the reaction mixture was stirred at room temperature for 40-45 min and concentrated in vacuo. The mixture was diluted with about 75 mL of water and acidified to pH 2 with 0.1 N HCl and the resulting oil was dissolved in ethyl acetate (300 mL). The EtOAc was washed with saturated NaCl solution (2×100 mL), dried over MgSO$_4$, filtered and the solvent was evaporated in vacuo to give the solid amino acids, the properties of which are given below.

5,6-DM-Bsmoc-Asn(Trt)-OH

Evaporation of ethyl acetate and then recrystallization from hot ethyl acetate gave 17.94 g (70.0%) of the acid as a white solid, m.p. 215-220° C.; $^1$H NMR (DMSO-d$_6$): δ 2.68 (d, 2), 3.8 (d, 6), 4.29 (q, 1), 4.98 (q, 2), 6.96-7.27 (m, 16+), 7.39 (s, 1), 7.55 (s, 1), 7.72 (d, 1, NH), 8.64 (s, 1). Anal. Calcd for C$_{35}$H$_{32}$N$_2$O$_9$S: C, 64.01; H, 4.91; N: 4.27. Found: C, 63.72; H, 4.99; N, 4.25.

5,6-DM-Bsmoc-Gln(Trt)-OH

Evaporation of ethyl acetate and then recrystallization from hot ethyl acetate gave 19.63 g (75.0%) of the acid as a white solid, m.p. 224-226° C.; $^1$H NMR (DMSO-d$_6$): δ 1.72 (m, 1), 1.93 (m, 1), 2.37 (m, 2), 3.83 (d, 6), 3.97 (distorted sextet, 1), 4.98 (q, 2), 7.15-7.28 (m, 16+), 7.38 (s, 1), 7.52 (s, 1), 7.72 (d, 1, NH), 8.60 (s, 1). Anal. Calcd for C$_{36}$H$_{34}$N$_2$O$_9$S: C, 64.47; H, 5.11; N: 4.18. Found: C, 64.29; H, 5.18; N, 4.16.

5,6-DM-Bsmoc-Leu-OH

Evaporation of ethyl acetate gave 11.3 g (70.2%) of the acid as a yellow amorphous solid, m.p. 81-91° C.; $^1$H NMR (DMSO-d$_6$): δ 0.85 (d, 3), 0.88 (d, 3), 1.42-1.68 (m, 3), 3.86 (s, 3), 3.87 (s, 3). 3.97 (m, 1), 4.96 (q, 2), 7.26 (s, 1), 7.53 (s, 1),7.73 (s, 1). HRMS: [M]$^+$ calcd for C$_{18}$H$_{23}$NO$_8$S: 413.1144; obsd: 413.1160.

EXAMPLE 12

General Procedure for the Preparation of 5,6-Dimethoxy-1,1-dioxobenzo[b]thiophene-2-methoxycarbonyl Amino Acids Using Dmoc-OSu in Acetonitrile-Water in the Presence of Triethylamine. Method B To a suspension of 12.8 mmol of an amino acid in 50 mL of acetonitrile/water (1/1) was added an amount of triethylamine to give an apparent pH of 9. The suspension became clear. 5,6-DM-Bsmoc-OSu (5 g, 12.8 mmol) was added in one portion and the pH was kept at 8.5-9.0 by adding triethylamine if necessary. The IR spectrum after 5 min showed the complete disappearance of the OSu derivative and the reaction mixture was stirred for additional 10 min. Concentrated HCl was added to pH 2 and the mixture was extracted with 2×35 ml of EtOAc and the EtOAc evaporated at reduced pressure (at this point the crude product was about 79% pure). The residue was redissolved in water (70-140 ml) and 3.5 g of K$_2$CO$_3$ and extracted with 3×25-40 ml of EtOAc and discarded. The aqueous layer was acidified with concentrated HCl to pH 2 and extracted with 3×25-40 ml of EtOAc. The organic layer was dried over MgSO$_4$, filtered and evaporated at reduced pressure to give a product which was triturated with ether and filtered.

5,6-DM-Bsmoc-Arg(Pbf)-OH

Evaporation of EtOAc and trituration with ether gave 7.0 g (77.17%) of the acid as a white solid. m.p. 135-155° C. dec.; IR (NaCl): 1136, 1307 (SO$_2$), 1726 (CO, acid; urethane) cm$^{-1}$; $^1$H NMR (CDCl$_3$): δ 1.4 (s, 6), 1.60-1.9 (m, 4), 2.01 (s, 3), 2.45-2.51 (2 s, 6), 2.91 (s, 2), 3.19 (bs, 2), 3.87 (s, 3), 3.90 (s, 3), 4.29 (m, 1), 5.03 (q, 2), 6.40 (d, 2), 6.83 (s, 1), 7.10 (s, 1), 7.13 (s, 1). $^{13}$C-NMR (DMSO, d$_6$, 75 MHz): δ 12.32, 17.65, 19.01, 28.32, 42.51, 53.80, 55.82, 56.16, 56.44, 86.36, 105.17, 108.91, 116.35, 123.33, 124.40, 128.31, 130.52, 131.51, 134.19, 137.35, 138.06, 150.64, 152.82, 155.58, 156.14, 157.52, 137.62. HRMS: [M+H]$^+$ calcd for C$_{31}$H$_{40}$N$_4$O$_{11}$S$_2$: 709.2208; obsd: 709.2176

5,6-DM-Bsmoc-His(Trt)-OH

After acidification to pH 2 some of the acid (2.3 g) separated and was filtered. Extraction of the aqueous layer with EtOAc followed by drying, evaporation and trituration with ether gave an additional 3.9 g. The combined amount of the acid (6.2 g, 71.26%) was obtained as a white solid. m.p. 145-160° C. dec (gas evolved); IR (NaCl): 1136, 1307 (SO$_2$), 1726 (CO, acid; urethane) cm$^{-1}$; $^1$H NMR (CDCl$_3$): δ 3.6 (dd, 2), 4.24 (s, 6), 4.82 (q, 1), 5.26 (q, 2), 6.4 and 6.75 (2d, NH), 7.19 8.39 (m, 20). $^{13}$C-NMR (CDCl$_3$, 75 MHz): δ 28.31, 54.23, 56.45, 56.56, 77.43, 104.30, 108.15, 121.48, 124.13, 127, 87, 127.93, 128.65, 128.84, 128.95, 131.71, 135.67, 138.65, 140.18, 150.47, 153.05, 155.14, 173.24. HRMS: [M+H]$^+$ calcd for $C_{37}H_{33}N_3O_8S$: 680.2061; obsd: 680.2066.

EXAMPLE 13

Preparation of Ethyl 5-(methylthio)benzo[b]thiophene-2-carboxylate

Two hundred and fifty grams (1.23 moles) of 5-(methylthio)benzoic acid was added portionwise to 600 ml of thionyl chloride over a period of 30 minutes and the resulting reaction mixture was heated under reflux for about 4-5 h. Excess thionyl chloride was removed by distillation and the residue was redistilled under high vacuum to afford 203 g (75%) of the acid chloride as a liquid which crystallized on standing, mp 28-30° C.; $^1$H-NMR (400 MHz, CDCl$_3$): δ 2.53 (s 3), 7.34-7.40 (m 2), 7.88 (d 1); IR (DCM) 1772 cm$^{-1}$ (C=O). The crude acid chloride was used as such in the next step. In a 2-l three-necked, round-bottomed flask equipped with a mechanical stirrer and thermometer there was introduced 700 ml of dry acetonitrile followed by 4.41 g (0.11 moles) of NaBH$_4$ and the mixture stirred for 10 min to allow partial dissolution of the borohydride reagent. The mixture was cooled to between 0 and −5° C. and 17.9 g of a cadmium chloride/DMF complex [Johnstone, et al. *J. Chem. Soc. Chem. Comm.* 354 (1978)] [CdCl$_2$×1.5 DMF] was added in one portion. The white suspension was agitated for 5 min, and cooled to −20-25° C. A solution of 26.5 g (0.12 moles) of 2-chloro-5-(methylthio)benzoyl chloride in 400 ml of acetonitrile was cooled to about −15° C. and quickly added to the CdCl$_2$ suspension described above. The mixture was stirred for 3 min between −20 and −25° C. and thereafter the reaction was quenched by the addition of 400 ml of dilute hydrochloric acid (10%). A small amount of solid was removed by filtration and the filtrate was concentrated with a rotary evaporator. The residue was extracted with ethyl ether (3×100 ml) and the ether layer washed with 10% NaHCO$_3$ and brine. The organic phase was shaken overnight with 150 ml of aqueous 40% sodium bisulfite and the precipitated bisulfite adduct was filtered, washed with ether and dried in vacuo to give 24 g (69%) of adduct as a white solid. The aldehyde was regenerated by treatment of the adduct with 200 ml of 10% sodium carbonate in water for 2 h. The suspension was extracted with ethyl ether (3×60 ml) and the organic layer dried over MgSO$_4$. After removal of solvent with a rotary evaporator 13.5 g (61%) of the pure aldehyde was obtained as a white solid, mp 136-137° C.; $^1$H-NMR (200 MHz, CDCl$_3$): δ 2.51 (s 3), 7.28-7.8 (3), 10.44 (s, 1); IR (KBr): 1680 cm$^{-1}$ (CH=O). The crude aldehyde was used without further purification. A solution of 33 g (0.224 mole) of ethyl sodiomercaptoacetate in 250 ml of dry DMSO was added slowly at 75-85° C. under a nitrogen atmosphere to a solution of 22 g (0.117 moles) the crude aldehyde. After half of the sodiomercaptoacetate solution had been added 9.8 g of anhydrous K$_2$CO$_3$ was added in one portion and the addition of the sodiomercaptoacetate solution completed. The reaction mixture was kept at 80° C. for about 20 h, then cooled in an ice bath and poured into 1.5 l of ice cold dilute hydrochloric acid. The product was isolated by extraction into ethyl acetate followed by solvent evaporation with a rotary evaporator and recrystallization from ethyl acetate/hexane to give 19 g (65%) of the ester as a yellow solid, mp 44-46° C., $^1$H-NMR (200 MHz, CDCl$_3$): δ 1.41 (t, 3), 2.5 (s, 3), 4.39 (q, 2), 7.96 (s, 1), 7.7 (d, 1), 7.36 (dd 1), 7.74 (d, 1) IR (KBr): 1708.7 cm$^{-1}$ (CH=O).

EXAMPLE 14

Preparation of 5-(Methylthio)benzo[b]thiophene-2-methanol

To a suspension of 10 g of LiAlH$_4$ in dry ether (300 ml) was added dropwise under a N$_2$ atmosphere a solution of 34 g (0.13 moles) of ethyl 5-(methylthio)benzo[b]thiophene-2-carboxylate dissolved in the minimum amount of ethyl ether (ca 350 ml). The reaction mixture was monitored by TLC (ethyl acetate/hexane) and stirred at room temperature until starting materials disappeared (2 h). Excess of LiAlH$_4$ was decomposed by the addition of a solution prepared from 60 mL of ethyl acetate in 500 ml of ether. After the violent reaction had subsided 50-60 ml of water was added carefully. When the mixture became white the salts which had separated were dissolved in 75 mL of 40% H$_2$SO$_4$ and 500 mL of water. The organic layer was separated and the aqueous layer was extracted with ethyl ether (3×100 ml) and the combined organic layers were washed with sodium carbonate, water and brine and dried over sodium sulfate. The solvent was removed with a rotary evaporator and the residue was recrystallized from ethyl acetate/hexane to give 20 g (75%) of the sulfide alcohol, mp 112-113° C.; $^1$H-NMR (200 MHz, CDCl$_3$): δ 2.55 (s, 3), 4.93 (s, 2), 7.27 (dd, 1), 7.62 (d, 1), 7.36 (dd, 1), 7.72 (d, 1); $^{13}$C-NMR (75 MHz, DMSO): δ 15.26, 59.26, 119.73, 120.81, 123.12, 123.34, 134.21, 136.15, 140.67, 149.13; IR (KBr): 3302 (OH), 1437.2 (C=C) cm$^{-1}$. Anal. Calcd. for $C_{10}H_{10}OS_2$: C, 57.14; H, 4.76. Found: C, 57.01; H, 4.7.

EXAMPLE 15

Preparation of 5-(Methylthio)benzo[b]thiophene-2-methyl Chloroformate

Liquid phosgene (8.5 ml, 371 mmoles) was collected in a condenser at −78° C. and added to a mixture of 30 ml of DCM and 10 ml of THF at −78° C. in a 500-ml, three-neck roundbottomed flask equipped with a magnetic stirrer and a dropping funnel. A solution of 2.5 g (12 mmoles) of 5-(methylthio)benzo[b]thiophene-2-methanol in a mixture of 40 ml of DCM and 20 ml of THF was introduced dropwise over a period of 30 min. The reaction mixture was allowed to warm to room temperature and stirred overnight. Excess phosgene was removed by a stream of nitrogen and application of a weak vacuum. Any remaining phosgene was destroyed by absorption into 40% aqueous KOH solution. After THF and DCM were removed by distillation (always in the hood for safety reasons) the residual solid was recrystallized from DCM/hexane to give 2.8 g (87%) of the chloroformate contaminated by small amounts of unknown materials; $^1$H-NMR (200 MHz, CDCl$_3$) δ 2.54 (s, 3) 5.51 (s, 2) 7.22-7.34 (m, 2), 7.66 (d, 1), 7.72 (d, 1); IR/KBr 1774 (C=O) cm$^{-1}$. The crude chloroformate was not further purified but used as such for the synthesis of amino acid derivatives.

EXAMPLE 16

Preparation of 5-(Methylthio)benzo[b]thiophene-2-methyl 4-Nitrophenyl Carbonate

A solution of 6.3 g (0.0312 mole) of p-nitrophenyl chloroformate in 200 ml of dry DCM was chilled to 0° C. and a solution of 6.3 g (0.03 mole) of 5-(methylthio)benzo[b]thiophene-2-methanol, 3.75 g of DMAP (0.031 mole) and 350 ml of DCM was slowly added with efficient stirring over a period of 30 min. The reaction mixture was stirred at 0° C. for 1 h and at room temperature for an additional 3 h. The reaction mixture was washed with 10 N HCl (3×50 ml), water (3×50 ml), brine (1×50 ml) and dried over $MgSO_4$. The solvent was removed in vacuo with the aid of a rotary evaporator and the residual solid was recrystallized from ethyl acetate/hexane to give 8.7 g (80%) of the carbonate as a pale yellow solid, mp 101-102° C.; $^1$H-NMR (200 MHz, $CDCl_3$) δ 2.54 (s, 3) 5.52 (s, 2) 7.26-7.41 (m, 4), 7.67 (d, 1), 7.64 (d, 1) 8.25 (td, 2); IR (KBr): 1768 (C=O), 1523 (NO2) $cm^{-1}$. Anal. Calcd for $C_{17}H_{13}NO_5S_2$: C, 54.40; H, 3.46; N, 3.73. Found: C, 54.41; H, 3.50; N, 3.55.

EXAMPLE 17

Preparation of 5-(Methylthio)benzo[b]thiophene-2-methoxycarbonyl Glycine t-Bu Ester To a mixture of 1.4 g (8.35 mmoles) of t-Bu glycinate hydrochloride in 75 ml of dry DCM was added at room temperature under stirring 2 g (16.36 moles) of DMAP. The stirring was continued for 5 min and then 3.1 g (8.26 mmoles) of 5-(methylthio)benzo[b]thiophene-2-methyl 4-nitrophenyl carbonate was added portionwise over a period of 15 min. The reaction mixture was stirred at room temperature overnight and then washed with 3×50-ml portions of sodium bicarbonate, cold water and brine and dried over sodium sulphate. The solvent was removed with a rotary evaporator and the residual solid purified by column chromatography. The elution of the column was first effected with DCM/hexane (1:1) until the first spot is removed and then with ethyl acetate/DCM (1:9). The second spot was collected and the solvent was evaporated to give 2.3 g (77%) of the t-Bu ester as a white solid, mp 55-57° C.; $^1$H-NMR (200 MHz, $CDCl_3$) δ 1.46 (s, 9) 2.53 (s, 3) 3.88 (d, 2) 5.33 (s, 2) 7.23 (d, 1), 7.27 (dd, 1), 7.63 (d, 1) 7.77 (d, 1); IR (KBr): 3340 (NH), 1743, 1698 (C=O) $cm^{-1}$. HR-FAB MS calcd. For $C_{17}H_{21}NO_4S_2$: 367.0912; found: 397.0930.

EXAMPLE 18

Preparation of 5-$MeSO_2$-Bsmoc-Gly-O-t-Bu

Oxidation of 5-(methylthio)benzo[b]thiophene-2-methoxycarbonyl glycine t-butyl ester was effected by means of MMPP according to a published procedure [Carpino et al. *J. Am. Chem. Soc.* 119, 9915, (1997)] using the following amounts of reagents: 2 g (5.45 mmoles) of the sulfide ester, 15 g of MMPP and 12 ml of water. The reaction mixture was stirred for 3 days at room temperature. After recrystallization from ethyl acetate/hexane there was obtained 1.8 g (76%) of the ester as a white solid, mp 152-153° C., $^1$H-NMR (200 MHz, $CDCl_3$) δ 1.47 (s, 9) 3.1 (s, 3) 3.89 (d, 2) 5.15 (d, 2) 7.21 (d, 1), 7.89 (d, 1), 7.93 (d, 1) 8.1 (dd, 1); IR (KBr): 3378 (NH), 1744, 1725 (C=O), 1311, 1153 ($SO_2$) $cm^{-1}$. HR-FAB MS calcd. For $C_{17}H_{21}NO_8S_2$: 454.0606; found: 454.0675.

EXAMPLE 19

Preparation of 5-$MeSO_2$-Bsmoc-Gly-OH

Deblocking of the t-Bu ester was carried out by means of 25% TFA in DCM. In a 100-mL flask, to a solution of 30 ml of 25% TFA in DCM, there was added in one portion with stirring 0.5 g (1.16 mmoles) of the corresponding ester. The mixture was stirred at room temperature overnight and after concentrating in vacuo treated with 100 ml of cold ethyl ether. The resulting solid was isolated by filtration and dried to give 0.4 g (93%) of the carboxylic acid as a white solid, mp 210-212° C. (dec); $^1$H-NMR (200 MHz, DMSO-$d_6$) δ 3.28 (s, 3) 3.55 (d, 2) 5.05 (s, 2), 7.16 (t, 1 NH), 7.9-8.24 (m, 4); $^{13}$C-NMR (75 MHz, DMSO-$d_6$) δ 42.53, 43.50, 56.24, 122.80, 124.95, 129.63, 130.32, 131.68, 140.65, 140.96, 146.29, 156.03, 171.70; $^{13}$C-NMR (DEPT-135 75 Mhz), δ 43.5, ($CH_3$), 42.53, 56.24, ($CH_2$), 122.80, 124.95, 129.63, 130.32 (CH); IR (KBr): 3379 (NH) 1741, (C=O), 1305, 1153 ($SO_2$) $cm^{-1}$. HR-FAB MS calcd. for $C_{13}H_{12}NO_8S_2$: 374.0004; found: 374.0053.

EXAMPLE 20

Preparation of 5-(Methylthio)benzo[b]thiophene-2-methoxycarbonyl Alanine

The alanine derivative was synthesized by adding portionwise to a mixture of 1 g (11.23 mmoles) of alanine and 1.2 g (10 mmol) of DMAP in 40 mL of acetonitrile/water (1:1) over a period of 30 min. 4.0 g of the nitrocarbonate. The reaction mixture was stirred overnight at room temperature and the yellow solution treated with 10.0 g of sodium dithonite and stirred until complete bleaching occurred. The colorless solution was acidified to pH 2 using 2N HCl and concentrated with a rotary evaporator. The resulting solid was extracted with ethyl acetate (4×100 ml). After crystallization from ethyl acetate/hexane there was obtained 2.8 g (86%) of the alanine derivative, mp 133-134° C. $^1$H-NMR (200 MHz, ($CDCl_3$+DMSO-$d_6$) δ 1.43 (d, 3) 2.50 (s, 3), 4.31 (q, 2), 5.33 (s, 1), 5.94 (d, 1), 7.23 (s 1), 7.26 (dd, 1), 7.61 (d, 1), 7.69 (d, 1); IR (KBr): 3337 (NH), 1723, 1691 (C=O) $cm^{-1}$. HR-FAB MS: calcd. for $C_{14}H_{15}NO_4S_2$: 325.0443; found: 325.0467.

EXAMPLE 21

Preparation of 5-$MeSO_2$-Bsmoc-Ala-OH

Oxidation of the sulfide was carried out by means of sodium perborate tetrahydrate according to the method used by Carpino et al. [*J. Org. Chem.*, 64, 4324 (1999)] for the oxidation of the benzo[b]thiophene moiety using the following amounts of reagents: 2 g (6.15 mmole) of the sulfide and 14 g (91.27 mmoles) of sodium perborate tetrahydrate in 100 ml of acetic acid. After recrystallization from ethanol/water there was obtained 1.8 g (75%) of the protected alanine as a white amorphous solid, $^1$H-NMR (200 MHz, $CDCl_3$) δ 1.45 (d, 3), 3.13 (s, 3), 4.31 (q, 2), 5.12 (s, 2), 6.21 (d, 2), 7.31 (s, 1), 7.92 (d, 1), 8.01 (d, 1), 8.12 (dd, 1); IR (KBr): 3316 (NH), 1733, 1707 (C=O), 1306 1157 ($SO_2$) $cm^{-1}$. HR-FAB MS: calcd. for $C_{14}H_{16}NO_8S_2$: 390.0317; found: 390.0354.

EXAMPLE 22

Preparation of 5-(Methylthio)benzo[b]thiophene-2-methoxycarbonyl Leucine

The leucine derivative was synthesized according to the procedure described for the glycine analog using the following amounts of reagents: 1.71 g (13.05 mmoles) of leucine, 1.6 g (13.1 mmoles) of DMAP and 4.9 g (13 mmoles) of the nitrophenyl carbonate in 100 ml of acetonitrile/water (1:1). After crystallization from ethyl acetate/hexane there was obtained 3.8 g (80%) of the leucine derivative as a white solid, mp 131-132° C.; $^1$H-NMR (200 MHz, CD$_3$CN) δ 0.91 (dd, 6) 1.58 (dt, 2), 1.96 (m, 1), 3.1 (s, 3), 4.07 (q, 1), 5.30 (d, 2), 6.01 (d, 1), 7.25-7.8 (m, 4); IR (KBr): 3338 (NH), 1717, 1665 (C=O) cm$^{-1}$. HRFAB MS: calcd. for C$_{17}$H$_{21}$NO$_4$S$_2$: 367.0912; found: 367.0934.

EXAMPLE 23

Preparation of 5-MeSO$_2$-Bsmoc-Leu-OH

Oxidation of the sulfide was carried out using the same method described for the alanine derivative. The protected amino acid was obtained as a white amorphous solid showing no distinct melting point, $^1$H-NMR (200 MHz, CD$_3$CN) δ 0.91 (dd, 6) 1.59 (dt, 3), 1.94 (m, 1), 2.52 (s, 3), 4.16 (q, 1), 5.08 (d, 2), 6.14 (d, 1), 7.38 (d, 1), 7.96 (d, 1), 8.03 (d, 1), 8.10 (dd, 1); IR (KBr): 3284 (NH), 1751, 1695 (C=O), 1308 1152 (SO$_2$) cm$^{-1}$. HRFAB MS: calcd. for C$_{17}$H$_{22}$NO$_8$S$_2$: 432.0787; found: 432.0749.

EXAMPLE 24

Preparation of 5-Nitrobenzo[b]thiophene-2-methanol

To a suspension of 10 g of NaBH$_4$ in 150 ml of dry dioxane was added portionwise 11.5 g (0.0476 moles) of 5-nitrobenzo[b]thiophene-2-carboxylic acid chloride [Lewis, J. J.; Martin-Smith, M.; Muir, T. C.; Nanjappa, S. N.; Reid, S. T. *J. Med. Chem.*, 6, 711 (1963).]. The mixture was heated under reflux for 5-10 min and then allowed to stand at room temperature for one hour. The excess sodium borohydride was decomposed with water and dilute hydrochloric acid and the reaction mixture diluted with 1 l of water. The resulting solid was isolated by filtration, dried and recrystallized from ethyl acetate/hexane (2:3) which gave 7 g (71%) of nitro sulfide alcohol, mp 126-127° C.; $^1$H-NMR (300 MHz, DMSO): δ 4.78 (s 2), 7.5 (s 1), 8.1 (dd 1), 8.19 (d 1), 8.71 (d 1); 13C NMR (75 MHz, DMSO): δ 58.65, 117.76, 118.70, 120.39, 123.54, 139.48, 144.91, 145.07, 151.96; IR (KBr): 3294 cm$^{-1}$ (OH), 1510, 1344 (NO2) cm$^{-1}$. Anal. Calcd. for C$_9$H$_7$NO$_3$S: C, 51.67; H, 3.34; N, 6.69. Found: C, 51.55; H, 3.45; N, 6.57.

EXAMPLE 25

Preparation of 5-Nitrobenzo[b]thiophenesulfone-2-methanol

Method A. A solution of 4.8 g (0.023 moles) of 5-nitrobenzo[b]thiophene-2-methanol in 500 ml of methanol was cooled to 0° C. and then 19 g of monoperoxyphthalic acid magnesium salt hexahydrate was added along with 15 ml of water. The mixture was stirred at room temperature until oxidation was complete (5-6 days). The reaction was monitored by TLC and when complete the white solid was filtered and discarded. The methanol was removed with a rotary evaporator and the resulting solid recrystallized from aqueous ethanol to give 3.7 g (67%) of the nitro sulfone alcohol, mp 172.5-174° C.; $^1$H-NMR (300 MHz, DMSO): δ 4.8 (d 2), 7.48 (s 1), 8.13 (d 1), 8.36 (dd 1), 8.46 (d 1); $^{13}$C NMR (75 MHz, DMSO): δ 54.16, 120.45, 122.52, 124.97, 125.5, 132.75, 141.65, 146.9, 151.10; IR (KBr): 3556 cm−1 (broad OH), 1302, 1156 cm−1 (SO$_2$) 1537, 1352 (NO$_2$) cm$^{-1}$. Anal. Calcd. for C$_9$H$_7$NO$_5$S: C, 44.81; H, 2.90; N, 5.80. Found: C, 44.71; H, 2.84; N, 5.71.

Method B. Oxidation was carried out according to a published procedure [Carpino, L. A.; Ismail, M.; Truran, G. A.; Mansour, E. M. E.; Iguchi, S.; Ionescu, D.; El-Faham, A.; Riemer, C.; Warrass, R. *J. Org. Chem.*, 64, 4324(1999)] using acetic acid and sodium perborate as the oxidizing agent, specifically 2.5 g (0.011 moles) of 5-nitrobenzo[b]thiophene-2-methanol, 10 g (0.064 moles) of sodium perborate tetrahydrate and 50 ml of acetic acid. After the reaction was complete half of the acetic acid was removed by distillation and the mixture poured into 500 ml of cold water. The resulting precipitate was isolated by filtration and then recrystallized from aqueous ethanol to give 1.8 g (69%) of the nitro sulfone alcohol which exhibited the same mp and $^1$H-NMR characteristics as the product obtained via method A.

Similar methods were used to prepare 5-chlorobenzo[b]thiophenesulfone-2-methanol, mp 120-121° C.; $^1$H-NMR (200 MHz, DMSO) δ 4.47 (s 2), 5.74 (t 1), 7.31 (d 1), 7.62 (dd 1), 7.74 (d 1), 7.90 (d 1); 6-chlorobenzo[b]thiophenesulfone-2-methanol, m.p. 141-142° C.; $^1$H-NMR (200 MHz, DMSO) δ 4.46 (d 2), 5.73 (t 1) 7.38 (d 1), 7.63 (d 1), 7.77 (dd 1), 8.12 (d 1) and 6-(methanesulfonyl)benzo[b]thiophenesulfone-2-methanol. m.p. 217-219° C.; $^1$H-NMR (400 MHz, DMSO): δ 3.36 (s 3), 4.53 (d 2), 5.81 (bs 1) 7.49 (d 1), 7.88 (d 1), 8.22 (dd 1), 8.42 (d 1).

EXAMPLE 26

Preparation of 3-methoxy-4-acetoxybenzaldehyde

A mixture of 100 g (657.28 mmol) of vanillin, 100 ml (1057.9 mmol) of acetic anhydride and 100 ml (1240.2 mmol) of pyridine was stirred at room temperature for 24 hours. The solvent was removed under reduced pressure and then 100 ml of toluene was added and the solvent again evaporated. The residual oil was redissolved in 400 ml of chloroform and washed with 3×50 ml of 10% CuSO$_4$ solution and 2×50 ml of water and 1×50 ml of saturated NaCl solution and dried over MgSO$_4$. Filtration and evaporation of the solvent gave 115 g (90%) of the aldehyde as an oil which solidified on standing. The crude material was highly pure according to $^1$H-NMR analysis and was used directly for the next step but a small sample was recrystallized from ether which gave a white solid, m.p 74-76° C. [lit. m.p. 76-77° C. J. Morey, J Chem. Ed., 65, 627, (1988)]; $^1$H-NMR (400 MHz, CDCl$_3$) δ 2.33 (s, 3), 3.89 (s, 3), 7.21 (d, 1), 7.48 (m, 2), 9.93 (s, 1).

EXAMPLE 27

Preparation of 2-bromo-4-acetoxy-5-methoxybenzaldehyde

Note: the method used was based on a procedure devised by Chen et al [*J. Am. Chem. Soc.* 136, 2583(2014)]. In a three neck round bottom flask fitted with a mechanical stirrer, dropping funnel and a thermometer there was added 165 g (1603.65 mmol) of NaBr and 2.5 L of water followed by the addition of 102.3 g (526.83 mmol) of 3-methoxy-4-acetoxybenzaldehyde. To the resulting suspension 33 ml (1280.3 mmol) of Br$_2$ was added dropwise at room temperature. The reaction mixture was stirred overnight to give an orange powder which was filtered and washed with 3 L of water and dried in the open air. There was obtained 112 g (77.7%) of the brominated aldehyde which was highly pure according to $^1$H-NMR analysis and used directly as such for the next step. Recrystalliztion from EtOH gave the bromobenzaldehyde as an off white solid. m.p 98-100° C. [lit. m.p, 101-103° C., J. Morey. J Chem. Ed., 65, 627, (1988)]; $^1$H-NMR (400 MHz, CDCl$_3$) δ 2.33 (s, 3), 3.87 (s, 3), 7.35 (s, 1), 7.5 (s, 1), 10.26 (s, 1).

EXAMPLE 28

Preparation of 2-bromo-4-hydroxy-5-methoxybenzaldehyde

In a three neck round bottom flask fitted with a mechanical stirrer and a condenser there was added 90.0 g (329.57 mmol) of 2-bromo-4-acetoxy-5-methoxybenzaldehyde, 44.8 g of KOH (87%, 695 mmol) and 400 ml of EtOH. The suspension was refluxed for 2 hours with stirring and then cooled in an ice bath and treated with 6N HCl until the pH dropped to 2. The precipitate was filtered and washed with cold water and dried in the open air to give 61.0 g (80%) of the crude hydroxy aldehyde which was highly pure according to $^1$H-NMR analysis and used directly as such for the next step. Recrystallization from EtOH gave the hydroxy aldehyde as tan colored crystals, m.p. 180-182° C. [lit. m.p. 179-180° C., J. Morey, *J Chem. Ed.* 65, 627, (1988)]; $^1$H-NMR (400 MHz, DMSO) δ 3.81 (s, 3), 7.12 (s, 1), 7.3 (s, 1), 9.98 (s, 1).

EXAMPLE 29

Preparation of 2-bromo-3-methoxy-4-(N,N-dimethylthiocarbamoyloxy)benzaldehyde

To a stirred solution of 2-bromo-4-hydroxy-5-methoxybenzaldehyde in 250 ml of DMF and 40 ml (40.72 g, 267.47 mmol) of DBU was added 34.77 g of N,N-dimethylthiocarbamoyl chloride portionwise over a period of 30 min. When the addition was complete the reaction mixture was stirred under N$_2$ over night. The mixture was poured into 1 L of water with rapid stirring which caused the separation of the crude thio ester as a light brown solid which after washing with water and drying in the open air gave 47.0 g (68.6%) of the crude ester, m.p. 142-143° C., which was highly pure according to $^1$H-NMR analysis and used directly as such for the next step. $^1$H-NMR (400 MHz, CDCl$_3$) δ 3.34 (s, 3), 3.44 (s, 3), 3.86 (s, 3), 7.34 (s, 1), 7.5 (s, 1), 10.26 (s, 1). ESI-HRMS: [M+Na]$^+$ calcd for C$_{11}$H$_{12}$BrNO$_3$S: 339.9613; obsd: 339.9596.

EXAMPLE 30

Preparation of 2-bromo-3-methoxy-4-(N,N-dimethylcarbamoylthio)benzaldehyde

A mixture of 20 g (62.85 mmol) of 2-bromo-3-methoxy-4-(N, N-dimethylthiocarbamoyloxy)benzaldehyde and 30 ml of diethylene glycol diethyl ether was heated to 200° C. for 3 hours, cooled to room temperature and 100 ml of cold water was added. The thioester which was precipitated was filtered and washed with water and dried in the open air to give 17.0 g (85%) of the crude thiobenzaldehyde as a brown solid which was highly pure according to $^1$H-NMR analysis and used as such for the next step. Recrystallization of a sample from EtOH gave light brown crystals, m.p. 139-141° C. $^1$H-NMR (400 MHz, CDCl$_3$) δ 3.02 (d, 6), 3.91 (s, 3), 7.44 (d, 1), 7.80 (s, 1), 10.29 (s, 1). ESI-HRMS: [M+Na]$^+$ calcd for C$_{11}$H$_{12}$BrNO$_3$S: 339.9613; obsd: 339.9594.

EXAMPLE 31

Preparation of 2-bromo-4-methylthio-5-methoxybenzaldehde

Note: the method was adapted from that of Sharon A. Bowden et al *Org. Proc. Res. Dev.,* 8, 33 (2004). A mixture of 4.6 g (14.5 mmol) of 2-bromo-3-methoxy-4-(N,N-dimethylcarbamoylthio)benzaldehde, 2.0 g of KOH (87%, 32 mmol) and 15 ml of MeOH was refluxed for 2 hours. The reaction mixture was then cooled in an ice bath to 0-5° C. and methyl iodide (2.28 g; 1 ml, 16.0 mmol) was added dropwise within 10 min. The reaction mixture was stirred at room temperature overnight to give a yellow precipitate and then 50 ml of water was added and the mixture filtered to give of 3.1 g (82%) the S-methyl aldehyde which was highly pure according to $^1$H-NMR analysis. Recrystallization of a sample from EtOH gave light brown crystals, m. p. 132-133° C., $^1$H-NMR (400 MHz, CDCl$_3$) δ 2.4 (s, 3), 3.92 (s, 3), 7.20 (s, 1), 7.29 (s, 1), 10.2 (s, 1). ESI-HRMS: [M+H]$^+$ calcd for C$_9$H$_9$BrO$_2$S: 260.9597; obsd: 260.9559.

EXAMPLE 32

Figure 2:
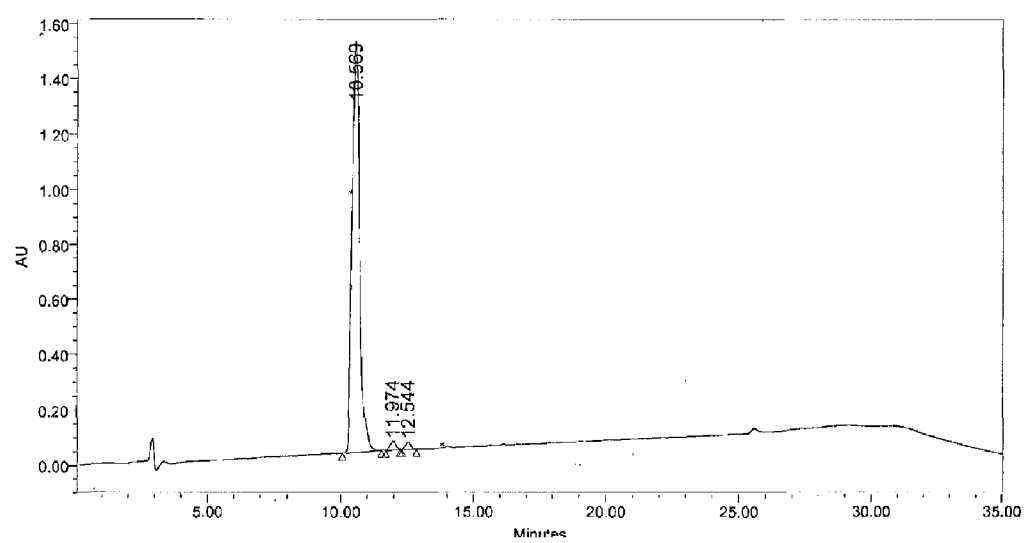
FIG. 2 is a graph for an HPLC trace for leucine enkephalin prepared via Dmoc chemistry.
Figure 3:
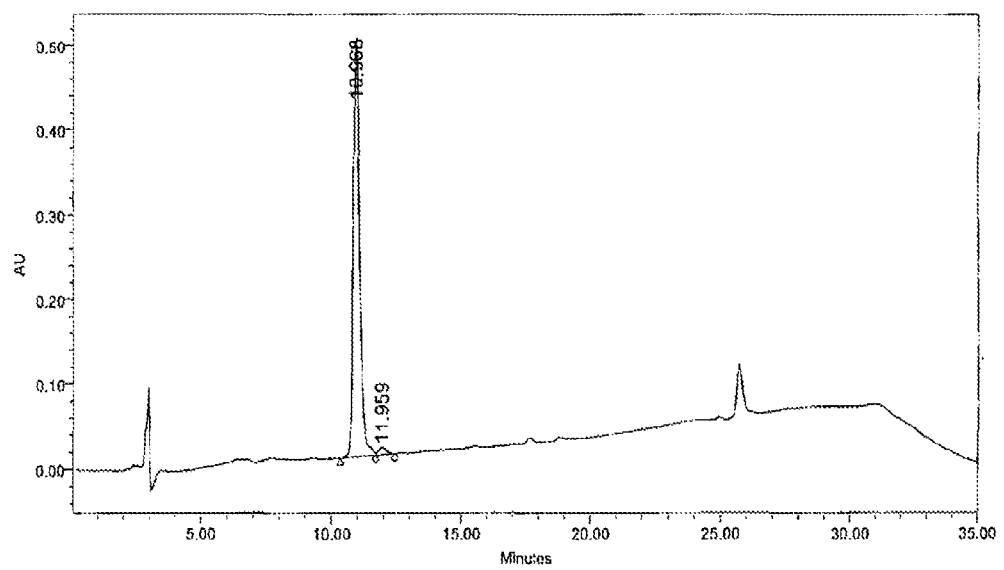
FIG. 3 is a graph for an HPLC trace for leucine enkephalin prepared via Fmoc chemistry.

Assembly of Lecuine Enkephalin and ACP$^{65-74}$ by SPPS via Dmoc Amino Acids and Comparison with the Assembly via Fmoc Amino Acids (A) Leucine Enkephalin The solid phase synthesis of leucine enkephalin (H-Tyr-Gly-Gly-Phe-Leu-NH$_2$) was performed manually using Dmoc chemistry. In a 5-ml fritted polypropylene syringe was placed 90 mg (0.065 mmol) of Rink Amide resin (a solid support) (loading 0.71 mmol/g, mesh size 200-400). The resin was swollen in DMF for 10 min and then washed with DMF, DCM and DMF 3×5 ml each. The solvents were removed using a water aspirator and the Fmoc protecting group attached to the resin was cleaved by 20% piperidine in DMF for 10 min and then the resin was washed with DMF, DCM and DMF 3×5 ml each. For the coupling step the protected amino acid (4 eq), N-HATU (4 eq), HOAt (4 eq) and DIEA (8 eq) were dissolved in 1 mL of DMF with the DIEA added last. Following dissolution the solution was added to the resin and the mixture agitated occasionally with a teflon rod for a period of 30 min. Deblocking was carried out similarly with 5 mL of 20% piperidine DMF. The resin was washed with DMF, DCM and DMF 3×5 ml each after each cycle of coupling and deprotection. Final cleavage of the peptide from the resin was performed by a 2-h treatment with 5 ml of 95% TFA and 5% H$_2$O. The TFA solution of the peptide was drained into a 100 ml flask and the syringe and the resin was washed with 5×5 ml of DCM and the washings added to the peptide solution in TFA. The solvent was removed in vacuo and the residue was washed with 3×15 ml of DCM to get rid of residual TFA. The peptide was precipitated by adding cold ether and centrifuged to give a white solid material which after drying weighed 25 mg (69.4%). HPLC analysis showed a major peak at 10.56 min. (purity 97.4%), An analogous Fmoc-based synthesis gave 28 mg (77.7%) at 10.96 min, (purity 97.8%). FIG. 2 shows the HPLC trace for leucine enkephalin prepared via Dmoc chemistry. FIG. 3 is a graph for an HPLC trace for leucine enkephalin prepared via Fmoc chemistry HPLC solvent system:

| Time | Flow | % A (1% TFA in H₂O) | % B (H₂O) | % C (MeCN) |
|---|---|---|---|---|
| 0.0 | 0.5 | 10.0 | 80.0 | 10.0 |
| 25 | 0.5 | 10.0 | 25.0 | 65.0 |
| 27 | 0.5 | 10.0 | 25.0 | 65.0 |
| 33 | 0.5 | 10.0 | 80.0 | 10.0 |
| 35 | 0.5 | 10.0 | 80.0 | 10.0 |

Column: XTerra C18. 3.5 μm; 4.6×100 mm

A low resolution mass spectrum via ESI gave the correct mass 555.30 (m+1) plus the dimer. The lack of a peak for m+Gly+1 demonstrates that no premature deblocking has occurred with the insertion of an extra glycine unit.

(B) ACP[65-74] (Acyl Carrier Protein (H-VAL-GLN-ALA-ALA-ILE-ASP-TYR-ILE-ASN-GLY-OH))

This synthesis was carried out by the same method described above for Leucine Enkephalin using both Fmoc and Dmoc amino acids The peptides were precipitated by adding cold ether and centrifuged to give white solid materials which after drying weighed 48 mg (70.5%) for Fmoc with purity 56.4% and 37 mg (54.4%) for Dmoc with purity 55.7%.

Figure 4:
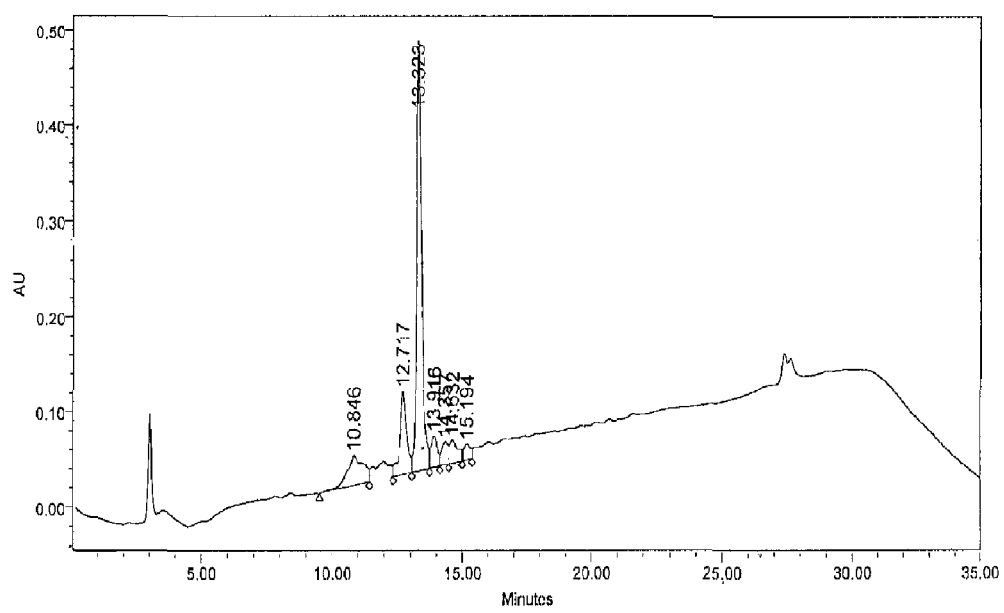
FIG. 4 is a graph for an HPLC trace for ACP$^{65-74}$ prepared via Dmoc chemistry.
Figure 5:
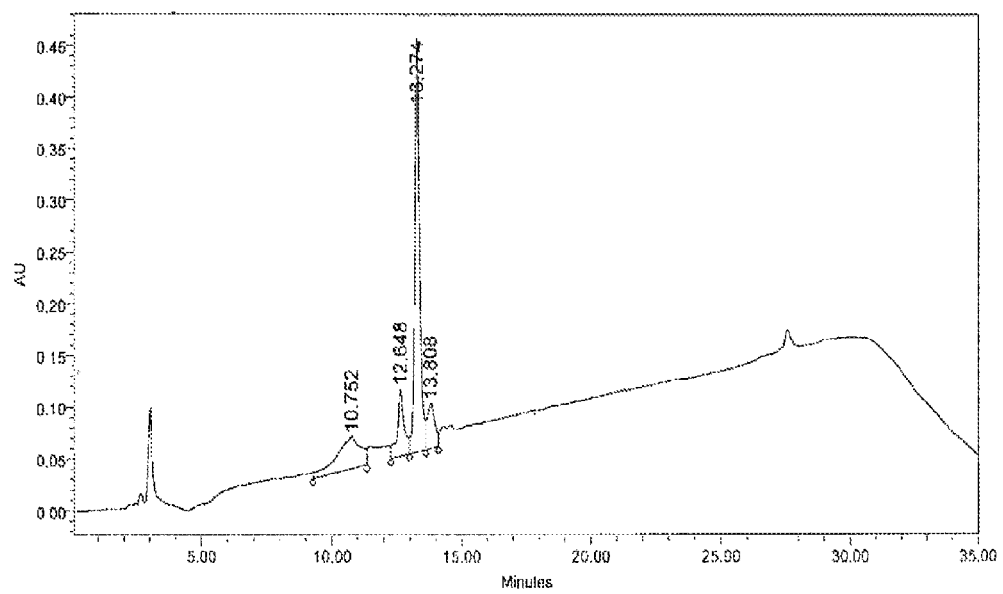
FIG. 5 is a graph for an HPLC trace for ACP$^{65-74}$ prepared via Fmoc chemistry.

FIG. 4 shows the HPLC trace for ACP[65-74] prepared via Dmoc chemistry. FIG. 5 shows the HPLC trace for ACP[65-74] prepared via Fmoc chemistry.

Having thus described certain embodiments of a DM-Bsmoc protecting group and related amino-protecting groups and method s of making the same, various alterations, modifications and improvements will be apparent to those of ordinary skill in the art. Such alterations, variations and improvements are intended to be within the spirit and scope of the application. Accordingly, the foregoing description is by way of example and is not intended to be limiting. The application is limited only as defined in the following claims and the equivalents thereto.

The invention claimed is:

1. An amino protecting group having a chemical formula of:
   5,6-dimethoxy-1,1-dioxobenzo[b]thiophene-2-methyl-oxycarbonyl (DM-Bsmoc).

2. An amino protecting group having a chemical formula of:

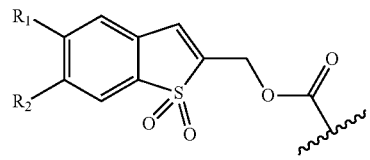

wherein $R_1$ and $R_2$ are one of the following:
$R_1$=MeO, $R_2$=OCH$_2$CH$_2$OMe
$R_1$=OCH$_2$CH$_2$OMe, $R_2$=MeO
$R_1$=MeO, $R_2$=OCH$_2$SO$_3$K
$R_1$=OCH$_2$SO$_3$K, $R_2$=MeO
$R_1$=MeO, $R_2$=MeO
$R_1$=MeSO$_2$, $R_2$=H
$R_1$=H, $R_2$=MeSO$_2$
$R_1$=$R_2$=MeSO$_2$
$R_1$=Me$_3$N$^+$, $R_2$=H
$R_1$=H, $R_2$=Me$_3$N$^+$
$R_1$=MeO, $R_2$=MeSO$_2$
$R_1$=MeSO$_2$, $R_2$=MeO
$R_1$=Cl, $R_2$=H
$R_1$=H, $R_2$=Cl
$R_1$=Cl, $R_2$=Cl.

3. The amino protecting group of claim 2, wherein $R_2$=MeSO$_2$.

4. The amino protecting group of claim 3, wherein $R_1$=MeO and $R_2$=MeSO$_2$.

* * * * *